(12) United States Patent
Farrell et al.

(10) Patent No.: US 11,338,109 B2
(45) Date of Patent: May 24, 2022

(54) HYDROPHILIC MEDICAL PRODUCTS AND HYDRATION MEDIUMS FOR HYDRATING THE SAME

(71) Applicant: Hollister Incorporated, Libertyville, IL (US)

(72) Inventors: David J. Farrell, Ballina (IE); Satwinder S. Panesar, Foxford (IE); Michael G. Murray, Ballina (IE); Vincent Naughton, Sligo (IE); Paul M. O'Donnell, Castlebar (IE); John P. O'Mahony, Ardnacrusha (IE); John T. Clarke, Galway (IE)

(73) Assignee: Hollister Incorporated, Libertyville, IL (US)

( * ) Notice: Subject to any disclaimer, the term of this patent is extended or adjusted under 35 U.S.C. 154(b) by 0 days.

(21) Appl. No.: 17/055,973

(22) PCT Filed: May 17, 2019

(86) PCT No.: PCT/US2019/032906
§ 371 (c)(1),
(2) Date: Nov. 16, 2020

(87) PCT Pub. No.: WO2019/222652
PCT Pub. Date: Nov. 21, 2019

(65) Prior Publication Data
US 2021/0275727 A1    Sep. 9, 2021

Related U.S. Application Data

(60) Provisional application No. 62/842,318, filed on May 2, 2019, provisional application No. 62/821,284, filed on Mar. 20, 2019, provisional application No. 62/821,268, filed on Mar. 20, 2019, provisional application No. 62/770,275, filed on Nov. 21, 2018, provisional application No. 62/739,449, filed on Oct. 1, 2018, provisional application No. 62/699,993, filed on Jul. 18, 2018, provisional application No. 62/672,755, filed on May 17, 2018.

(51) Int. Cl.
*A61L 29/04* (2006.01)
*A61L 29/14* (2006.01)
*A61M 25/00* (2006.01)
*A61M 25/01* (2006.01)

(52) U.S. Cl.
CPC ....... *A61M 25/0009* (2013.01); *A61L 29/043* (2013.01); *A61L 29/143* (2013.01); *A61L 29/146* (2013.01); *A61M 25/002* (2013.01); *A61M 25/0111* (2013.01); *A61L 2400/10* (2013.01)

(58) Field of Classification Search
CPC ............ A61M 25/0009; A61M 25/002; A61M 25/0111; A61L 29/043; A61L 29/143; A61L 29/146; A61L 2400/10
See application file for complete search history.

(56) References Cited

U.S. PATENT DOCUMENTS

| | | |
|---|---|---|
| 4,026,296 A | 5/1977 | Stoy et al. |
| 4,906,237 A | 3/1990 | Johansson et al. |
| 5,562,652 A | 10/1996 | Davis |
| 5,576,072 A | 11/1996 | Hostettler et al. |
| 5,616,119 A | 4/1997 | Davis |
| 5,876,663 A | 3/1999 | Laroussi |
| 6,120,904 A | 9/2000 | Hostettler et al. |
| 6,270,902 B1 | 8/2001 | Tedeschi et al. |
| 6,528,544 B2 | 3/2003 | Stern et al. |
| 6,629,961 B1 | 10/2003 | Israelsson et al. |
| 6,634,498 B2 | 10/2003 | Kayeroed et al. |
| 6,848,574 B1 | 2/2005 | Israelsson et al. |
| 6,923,936 B2 | 8/2005 | Swanson et al. |
| 6,986,868 B2 | 1/2006 | Madsen |
| 7,022,651 B1 | 4/2006 | Lightcap, Jr. et al. |
| 7,066,912 B2 | 6/2006 | Nestenborg et al. |
| 7,282,165 B2 | 10/2007 | Williams, III et al. |
| 7,476,223 B2 | 1/2009 | McBride |
| 7,569,155 B2 | 8/2009 | Schaefer |
| 7,833,475 B2 | 11/2010 | Madsen |
| 8,133,435 B2 | 3/2012 | Reynolds et al. |
| 8,177,774 B2 | 5/2012 | House |
| 8,267,919 B2 | 9/2012 | Utas et al. |

(Continued)

FOREIGN PATENT DOCUMENTS

| | | |
|---|---|---|
| EP | 1131112 B1 | 2/2003 |
| EP | 1312385 B1 | 2/2006 |
| EP | 1312385 B2 | 10/2009 |
| EP | 1714665 B1 | 8/2011 |
| EP | 2695636 A1 | 2/2014 |
| EP | 2550030 B1 | 4/2018 |
| EP | 3071249 B1 | 8/2018 |
| WO | 2002100455 A1 | 1/2002 |
| WO | 2004/075944 A2 * | 9/2004 |
| WO | 2005117914 A2 | 12/2005 |
| WO | 2016033234 A1 | 3/2016 |

(Continued)

OTHER PUBLICATIONS

International Search Report from Int. App. No. PCT/US2019/032892 dated Mar. 9, 2019.

(Continued)

*Primary Examiner* — Alma Pipic

(74) *Attorney, Agent, or Firm* — Cook Alex Ltd.

(57) ABSTRACT

Hydration mediums, assemblies containing hydration mediums and methods of making the same are disclosed. The hydration mediums are intended for hydrating or wetting a medical device such as a catheter and comprise a hydration foam. Furthermore, methods and products involving hydrophilic substances are disclosed e.g. involving mucilage, deep eutectic liquids, antifreeze substances or cryoprotectants, oil or a hydration medium together with water, surfactant, polyol and stabilizer.

24 Claims, 20 Drawing Sheets

(56) References Cited

U.S. PATENT DOCUMENTS

| | | |
|---|---|---|
| 8,608,689 B2 | 12/2013 | Scheller et al. |
| 8,703,048 B2 | 4/2014 | Nielsen et al. |
| 8,747,882 B2 | 6/2014 | Utas et al. |
| 8,747,911 B2 | 6/2014 | Gupta et al. |
| 8,871,869 B2 | 10/2014 | Dias et al. |
| 8,998,882 B2 | 4/2015 | Knapp et al. |
| 9,028,858 B2 | 5/2015 | Nielsen et al. |
| 9,138,510 B2 | 9/2015 | Madsen |
| 9,192,741 B1 | 11/2015 | Najibi |
| 9,220,866 B2 | 12/2015 | Van Groningen et al. |
| 9,408,946 B2 | 8/2016 | Utas et al. |
| 9,610,384 B2 | 4/2017 | Belt et al. |
| 9,801,979 B2 | 10/2017 | Utas et al. |
| 9,872,970 B2 | 1/2018 | Schønfeldt |
| 10,112,031 B2 | 10/2018 | Matthiassen |
| 10,245,355 B2 | 4/2019 | Ingber et al. |
| 10,328,237 B2 | 6/2019 | Kelly et al. |
| 10,398,161 B2 | 9/2019 | Arne et al. |
| 10,561,817 B2 | 2/2020 | Hannon et al. |
| 10,813,676 B2 | 10/2020 | Shimko et al. |
| 10,973,573 B2 | 4/2021 | Asirvatham et al. |
| 10,982,100 B2 | 4/2021 | Aizenberg et al. |
| 2002/0045049 A1 | 4/2002 | Madsen |
| 2002/0120333 A1 | 8/2002 | Keogh et al. |
| 2003/0065292 A1 | 4/2003 | Darouiche et al. |
| 2003/0124080 A1 | 7/2003 | Kawam et al. |
| 2003/0219475 A1 | 11/2003 | Truong-Le |
| 2004/0074794 A1 | 4/2004 | Conway et al. |
| 2004/0256264 A1 | 12/2004 | Israelsson et al. |
| 2005/0015076 A1 | 1/2005 | Giebmeyer et al. |
| 2005/0055044 A1 | 3/2005 | Kangas |
| 2005/0137582 A1 | 6/2005 | Kull-Osterlin et al. |
| 2005/0214376 A1 | 9/2005 | Faure et al. |
| 2006/0163097 A1 | 7/2006 | Murray et al. |
| 2007/0239107 A1 | 10/2007 | Lundberg et al. |
| 2007/0244449 A1 | 10/2007 | Najafi et al. |
| 2008/0142038 A1 | 6/2008 | Kunzler et al. |
| 2009/0012208 A1 | 1/2009 | Madsen et al. |
| 2009/0041727 A1 | 2/2009 | Suzuki et al. |
| 2009/0171317 A1 | 7/2009 | Versi |
| 2009/0221989 A1 | 9/2009 | Najafi et al. |
| 2009/0240214 A1 | 9/2009 | Conway et al. |
| 2010/0166809 A1 | 7/2010 | Northey et al. |
| 2010/0215643 A1 | 8/2010 | Clevenger et al. |
| 2010/0258568 A1 | 10/2010 | Frederiksen et al. |
| 2011/0114520 A1 | 5/2011 | Matthison-Hansen |
| 2011/0150961 A1 | 6/2011 | Perry et al. |
| 2011/0295239 A1* | 12/2011 | Gustavsson |
| 2012/0207853 A1 | 8/2012 | Alimi et al. |
| 2012/0289942 A1 | 11/2012 | Becker et al. |
| 2012/0316515 A1 | 12/2012 | Terry |
| 2013/0161208 A1 | 6/2013 | Gustavsson |
| 2014/0190846 A1 | 7/2014 | Belt |
| 2014/0271351 A1 | 9/2014 | Nielsen et al. |
| 2015/0065998 A1 | 3/2015 | Nielsen et al. |
| 2015/0238726 A1 | 8/2015 | Terry |
| 2015/0264935 A1 | 9/2015 | Chang |
| 2015/0335854 A1 | 11/2015 | Dvarsater et al. |
| 2016/0143944 A1 | 5/2016 | Panicheva et al. |
| 2016/0213880 A1 | 7/2016 | Oflynn et al. |
| 2017/0296609 A1 | 10/2017 | Ellington et al. |
| 2017/0296610 A1 | 10/2017 | Ellington et al. |
| 2017/0312484 A1 | 11/2017 | Shipley et al. |
| 2018/0000993 A1 | 1/2018 | Zhang |
| 2018/0010038 A1 | 1/2018 | Greenhill-Hooper et al. |
| 2018/0221541 A1 | 8/2018 | Pesika et al. |
| 2018/0258363 A1 | 9/2018 | Rhodes et al. |
| 2019/0001098 A1 | 1/2019 | Utas et al. |
| 2019/0083746 A1 | 3/2019 | Murray et al. |
| 2019/0105078 A1 | 4/2019 | Taylor et al. |
| 2019/0151610 A1 | 5/2019 | Fletter |
| 2019/0167849 A1 | 6/2019 | McBurney et al. |
| 2019/0201659 A1 | 7/2019 | Gustavsson et al. |
| 2019/0216735 A1 | 7/2019 | Venkatraman et al. |
| 2019/0216985 A1 | 7/2019 | McBurney et al. |
| 2019/0224384 A1 | 7/2019 | Lundahl et al. |
| 2019/0262647 A1 | 8/2019 | Havelka-Rivard et al. |
| 2019/0290805 A1 | 9/2019 | Kumaraswamy et al. |
| 2019/0290806 A1 | 9/2019 | Farrell et al. |
| 2020/0038535 A1 | 2/2020 | Montes De Oca et al. |
| 2020/0054795 A1 | 2/2020 | Farrell et al. |
| 2020/0146871 A1 | 5/2020 | Palmer |
| 2020/0206139 A1 | 7/2020 | Williams et al. |
| 2020/0222659 A1 | 7/2020 | Schertiger et al. |
| 2020/0338082 A1 | 10/2020 | Ackler |
| 2020/0345977 A1 | 11/2020 | Hickmott et al. |
| 2020/0391002 A1 | 12/2020 | Hilton et al. |
| 2020/0405919 A1 | 12/2020 | Van Weerd |
| 2021/0038508 A1 | 2/2021 | Binyamin et al. |

FOREIGN PATENT DOCUMENTS

| | | |
|---|---|---|
| WO | 2017001830 A1 | 1/2017 |
| WO | 2018028831 A1 | 2/2018 |
| WO | 2018029279 A1 | 2/2018 |

OTHER PUBLICATIONS

International Preliminary Report On Patentability from Int. App. No, PCT/US2019/032906 dated Nov. 17, 2020.

Written Opinion of the International Search Authority from Int. App. No. PCT/US2019/032892 dated Mar. 9, 2019.

International Search Report from Int. App. No. PCT/US2019/032906 dated Oct. 14, 2019.

Castro, V. I., Craveiro, R., Silva, J. M., Reis, R. L., Paiva, A., & C. Duarte, A. R. (2018). Natural deep eutectic systems as alternative nontoxic cryoprotective agents. Cryobiology, 83, 15-26.

European Examination Report dated Oct. 20, 2021 in EP19729966.2.

\* cited by examiner

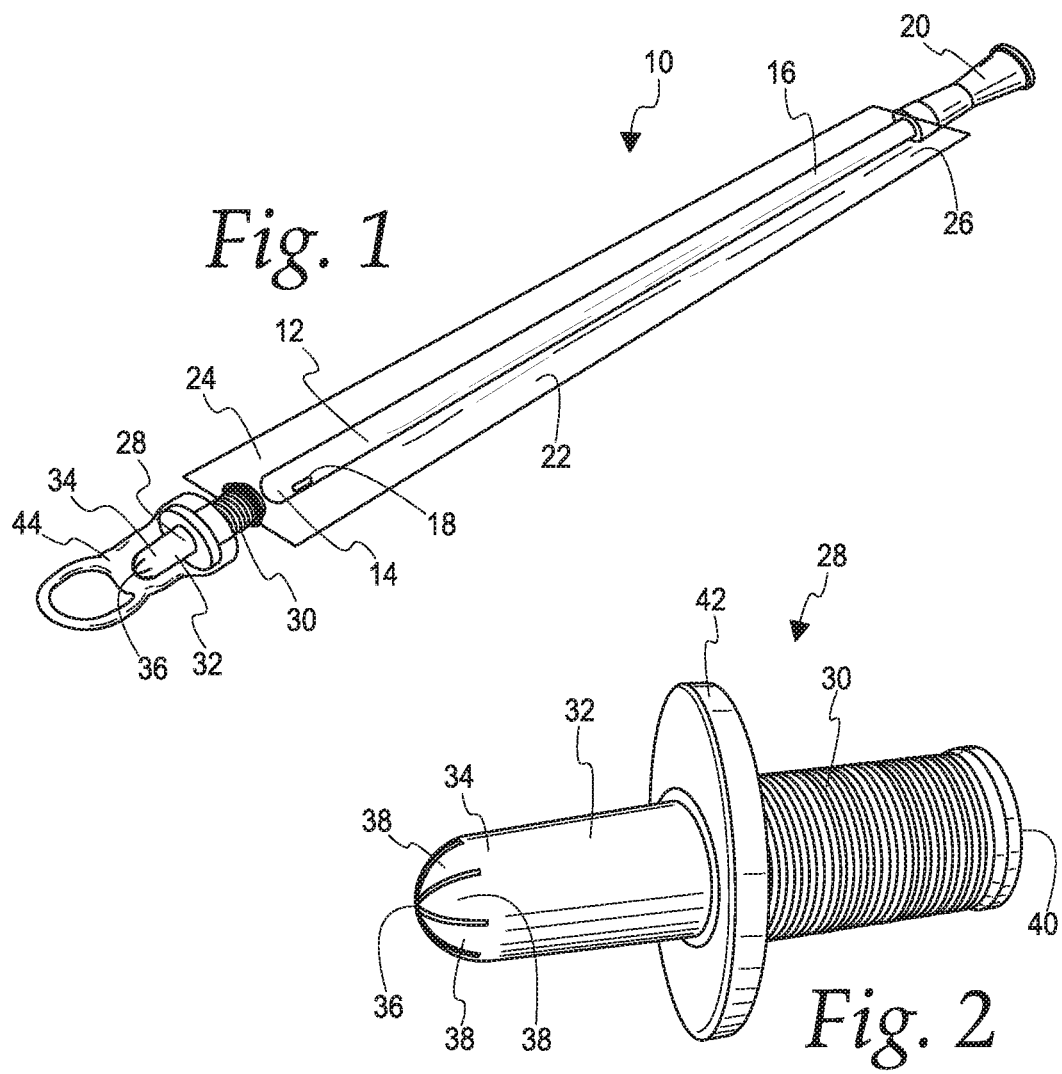
Fig. 1
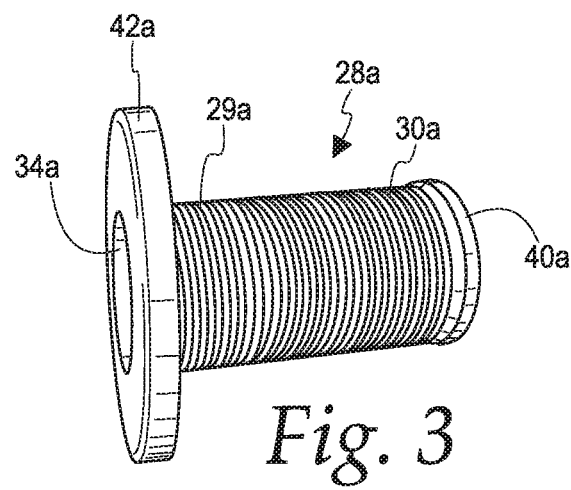
Fig. 2
Fig. 3

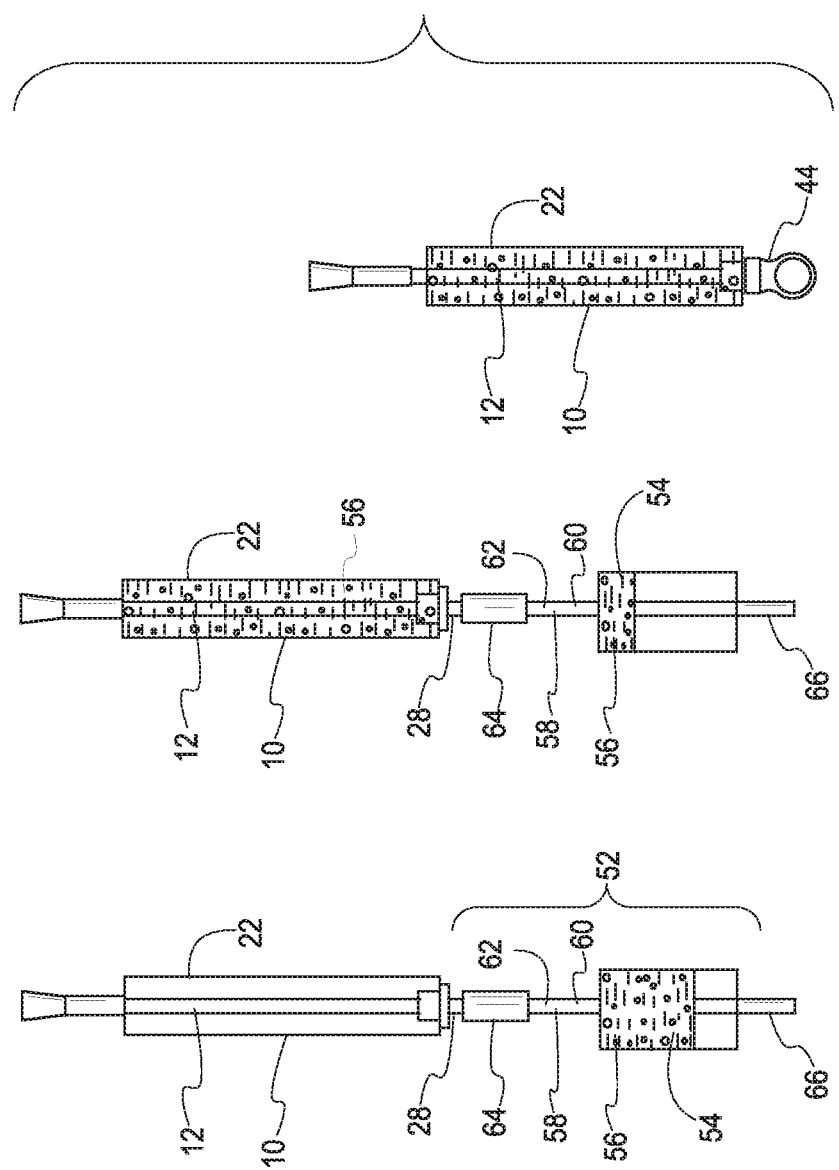

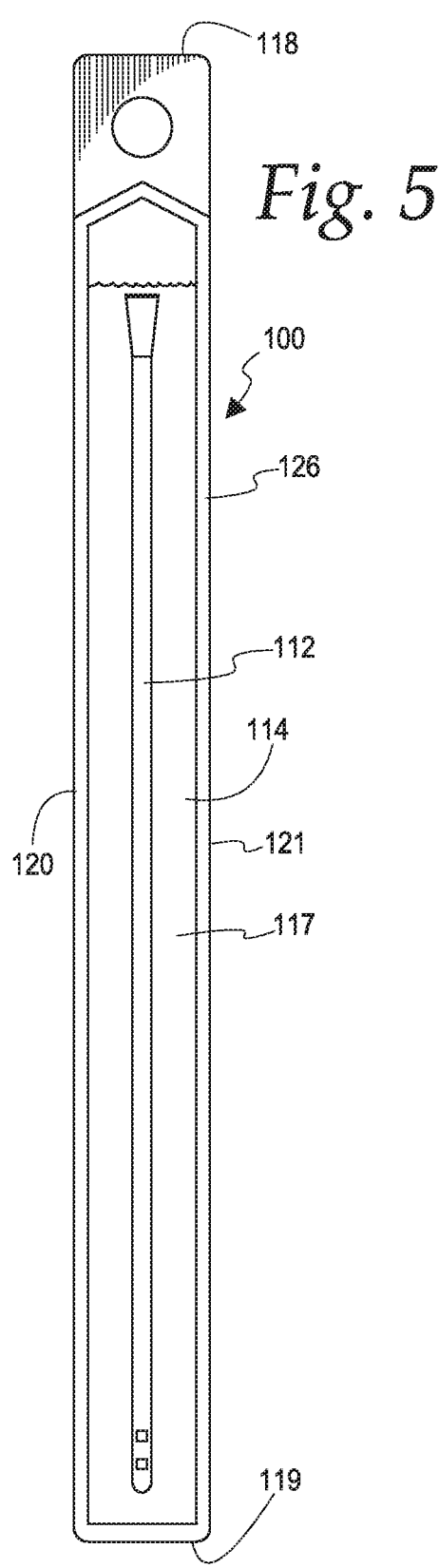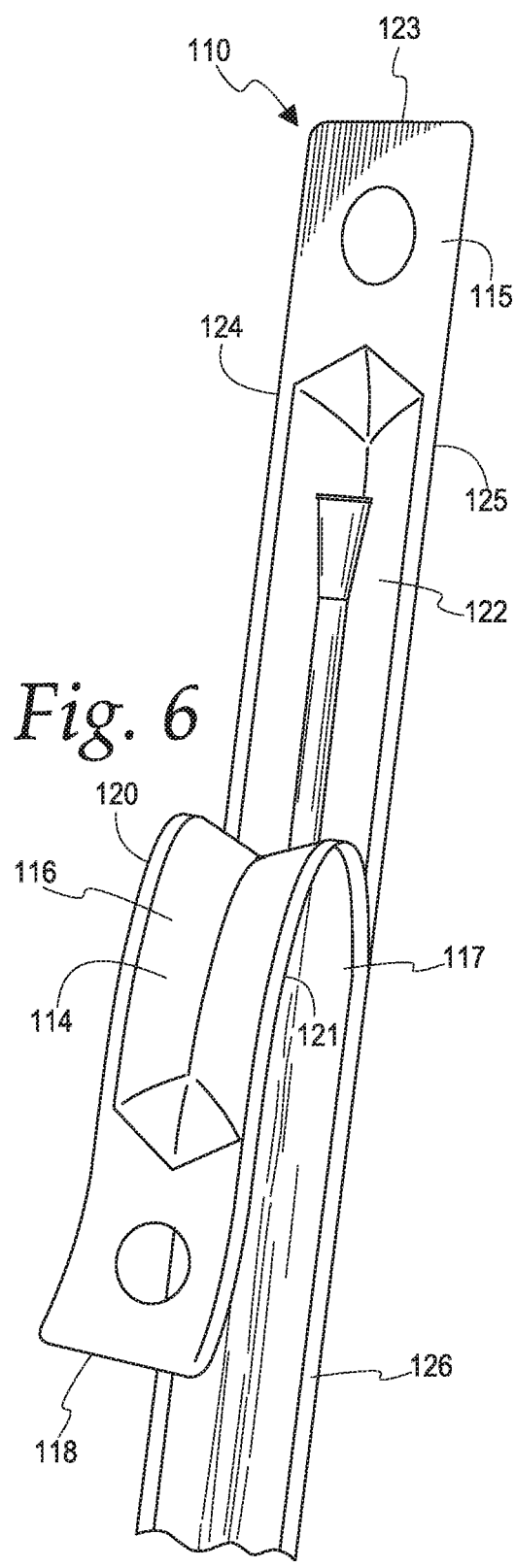

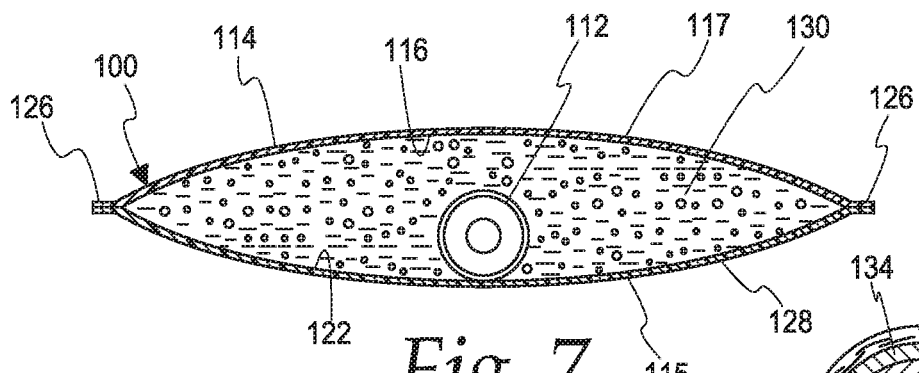
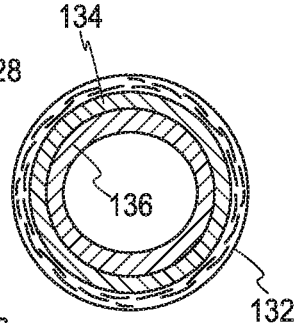
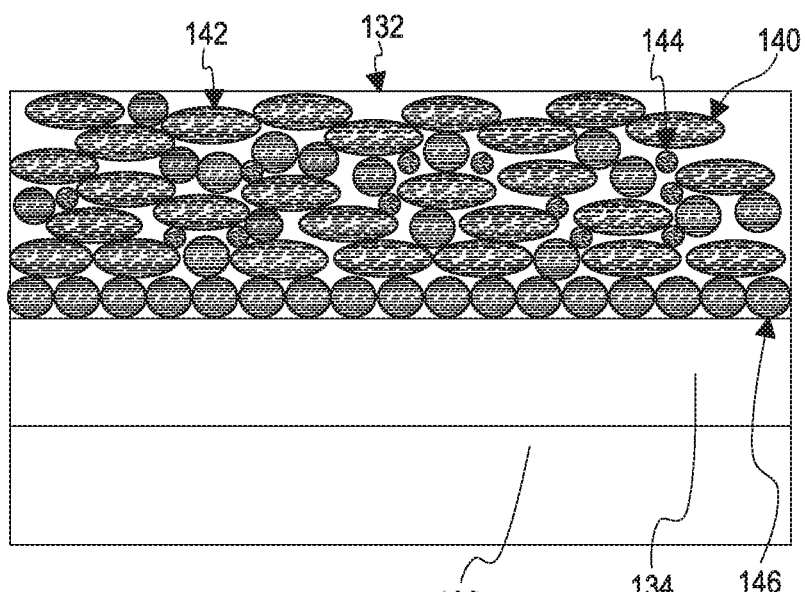
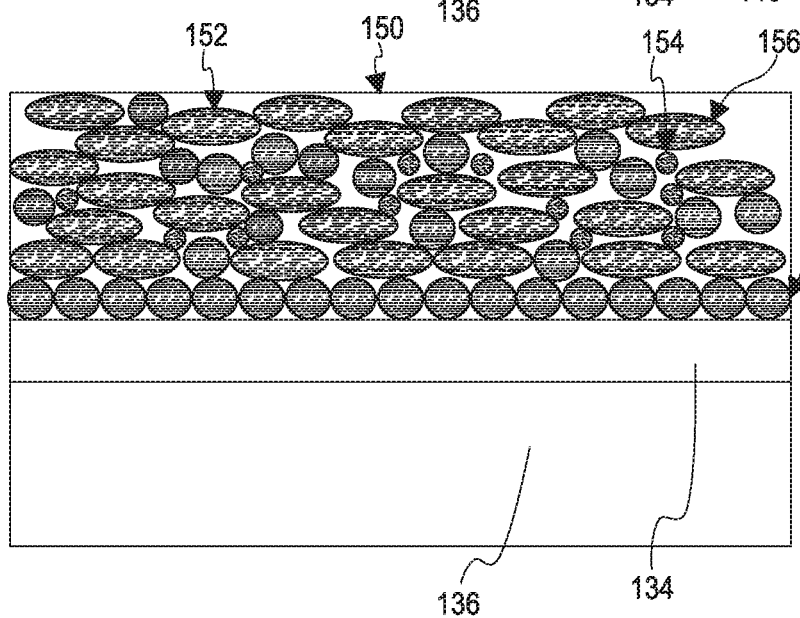

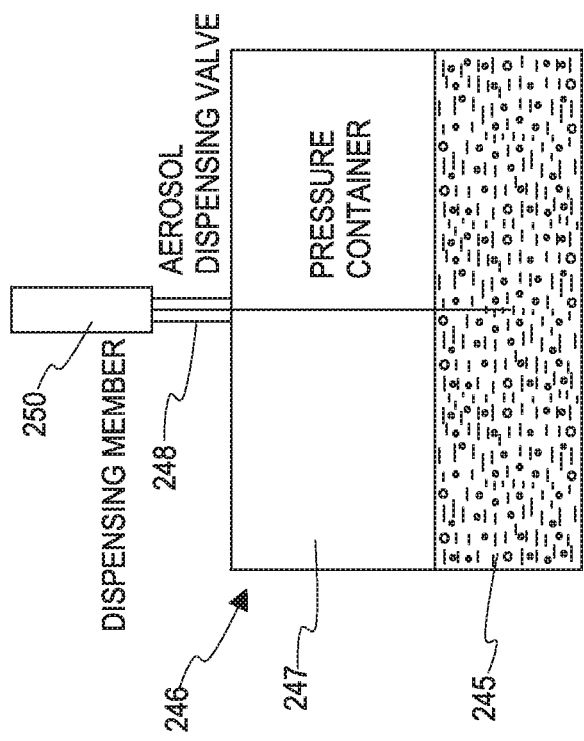
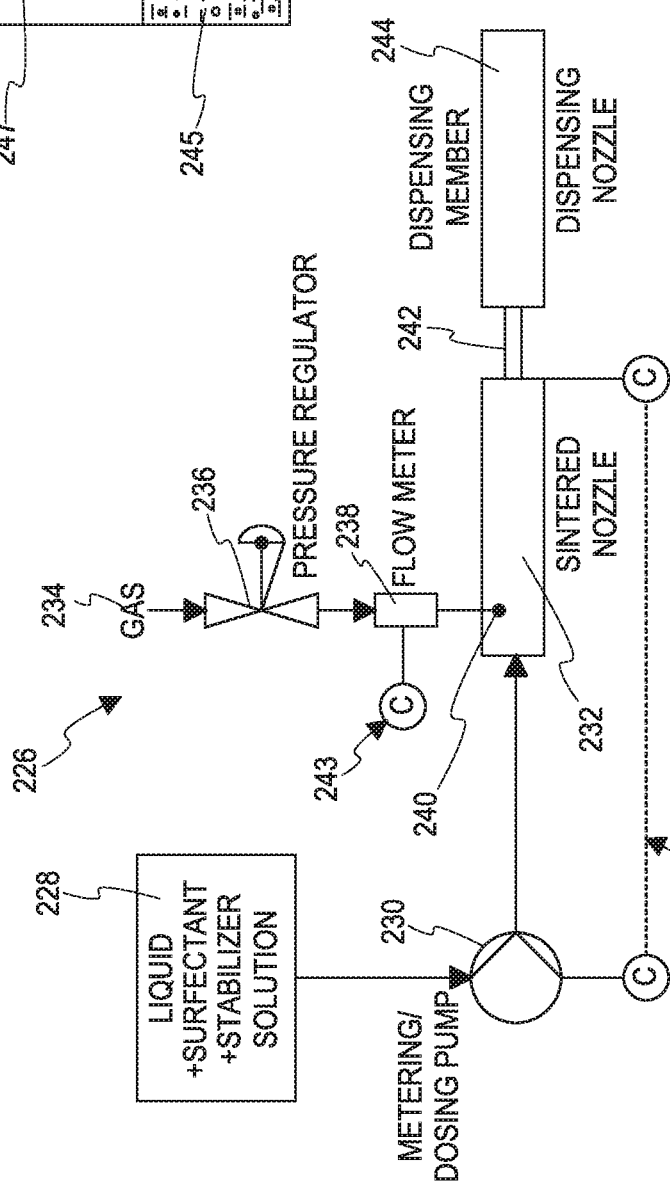

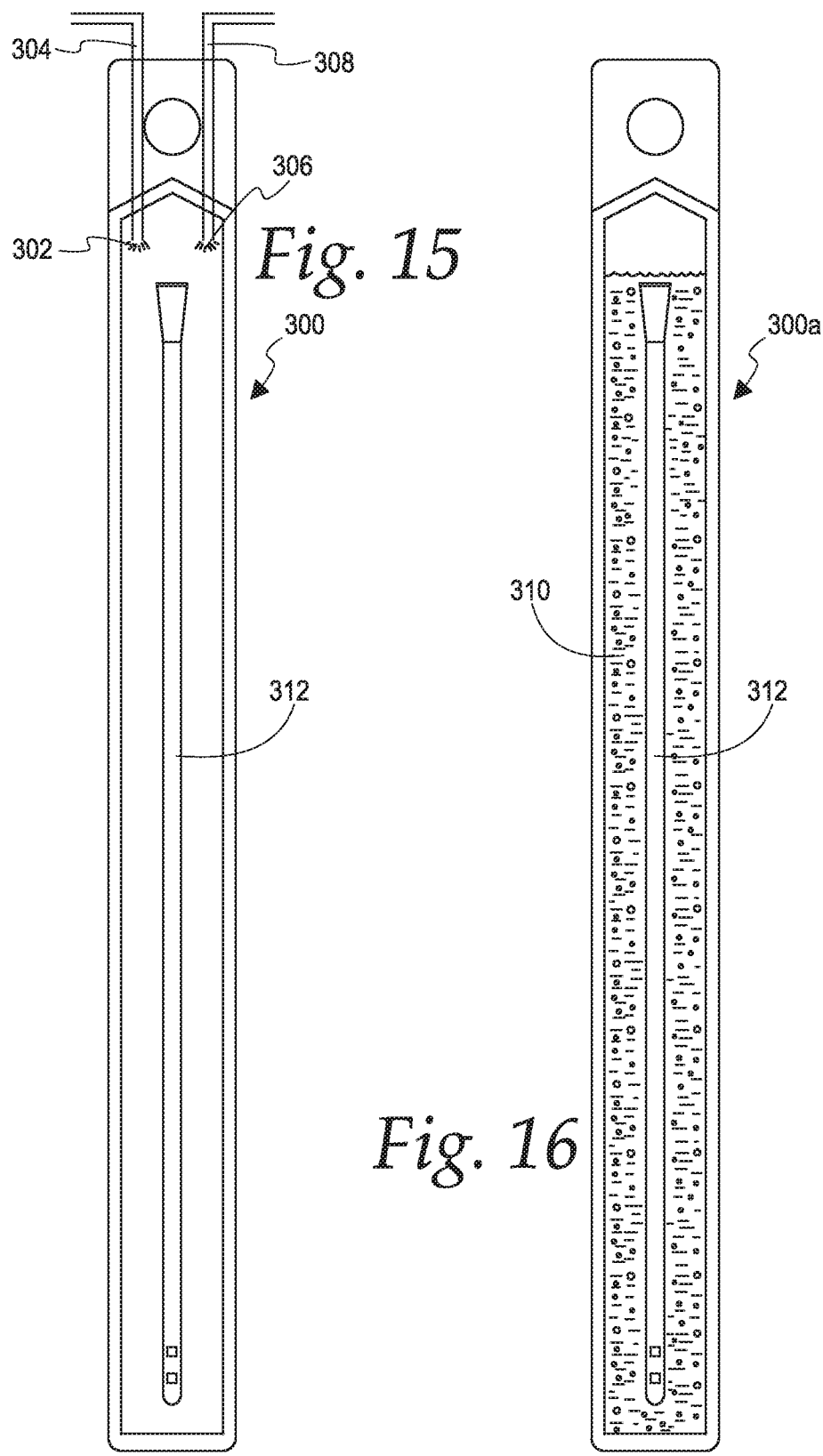

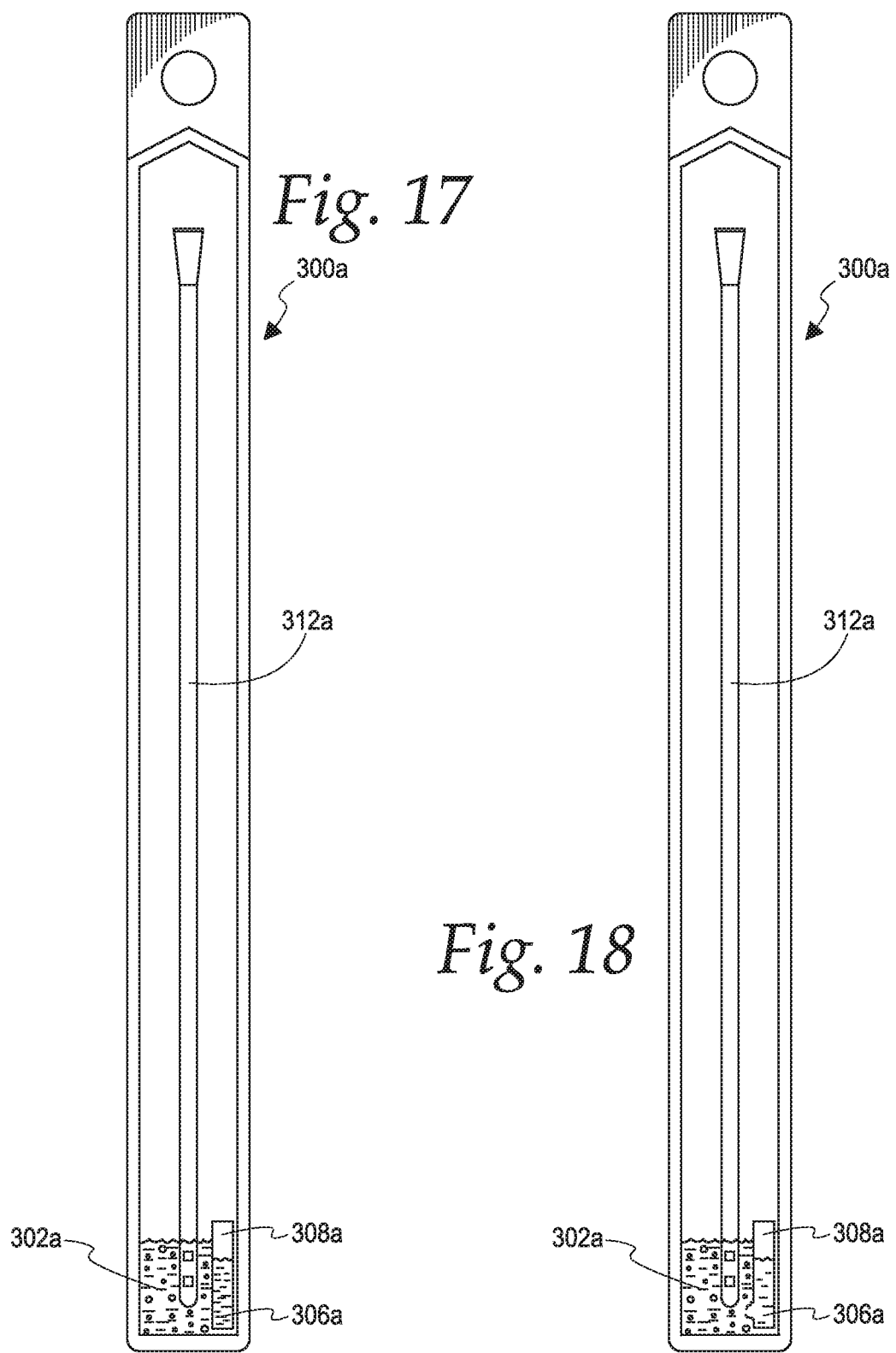

HYDROPHILIC MEDICAL PRODUCTS AND HYDRATION MEDIUMS FOR HYDRATING THE SAME

The present application is the U.S. National Stage of International Application No. PCT/US2019/032906, filed May 17, 2019, which claims the benefit and priority to U.S. Provisional Application No. 62/672,755, filed May 17, 2018, U.S. Provisional Application No. 62/699,993, filed Jul. 18, 2018, U.S. Provisional Application No. 62/739,449, filed Oct. 1, 2018, U.S. Provisional Application No. 62/770,275, filed Nov. 21, 2018, U.S. Provisional Application No. 62/821,268, filed Mar. 20, 2019, U.S. Provisional Application No. 62/821,284, filed Mar. 20, 2019, and U.S. Provisional Application No. 62/842,318, filed Mar. May 2, 2019, all of which are hereby incorporated herein by reference.

DESCRIPTION

Technical Field

The present disclosure generally relates to hydrophilic medical device products and hydration mediums for hydrating or wetting such medical devices. More particularly, the present disclosure generally relates to hydrophilic urinary catheter products and hydration mediums for hydrating such hydrophilic urinary catheters.

Background

Several different devices in different industries are required to be hydrated prior to use and/or stored in a hydrated condition. In many instances, such devices are stored or packaged in a hydration medium, such as a liquid hydration medium. Liquid hydration mediums may be, but are not limited to, water or aqueous solutions.

One type of device wherein it may be advantageous to package the device in a hydrated stated and/or in a hydration medium is a medical device that is made from a hydrophilic material, such as a hydrophilically coated urinary catheter. In several applications, a coating of hydrophilic material is applied to the surface of a device to provide a lubricious surface. When the hydrophilic material is wetted or hydrated with a hydration medium, the hydrophilic material becomes extremely lubricous. The hydration medium may be, for example, liquid or vapor water or an aqueous solution. In the field of insertable medical devices, the lubriciousness of the hydrophilic coating can ease introduction of the device into the body and aids in reducing pain and discomfort associated with such introduction.

In devices that are required to be stored in and/or hydrated with a hydration medium, the product may include a device that is packaged in an assembly with the hydration medium, such that the device is in contact with the hydration medium. In such packaging assemblies, if the assembly lacks a sufficient amount of hydration medium, the device may not be sufficiently hydrated for use. Even if a sufficient amount of hydration medium is placed in the package assembly, the packaging may be such that there is a risk that the device may not be evenly hydrated or that the hydration medium does not migrate in the package to hydrate the entire device. Alternatively, if too much hydration medium is placed in the package, there may be an increased risk of spillage when the package is opened. Additionally, too much hydration medium added to the package may result in some loss in efficiency of costs due to the cost associated with the excess hydration medium.

Therefore, there remains a need for package products that contain hydration mediums, methods of hydrating devices within a package with a hydration medium, and hydration mediums for use in such products and methods.

SUMMARY

There are several aspects of the present subject matter which may be embodied separately or together in the devices and systems described and claimed below. These aspects may be employed alone or in combination with other aspects of the subject matter described herein, and the description of these aspects together is not intended to preclude the use of these aspects separately or the claiming of such aspects separately or in different combinations as set forth in the claims appended hereto.

In one aspect, a hydration medium for hydrating or wetting a device, wherein the hydration medium comprising a hydration foam.

In another aspect, a product including a package containing the device and a hydration medium comprising a hydration foam.

In another aspect, a method of making a product that includes placing a device within a package, and placing a hydration medium into the package, wherein the hydration medium comprises a hydration foam.

In another aspect, a method of making a product includes mixing a gas and a hydration liquid to form a gas and liquid mixture. The gas and liquid mixture are formed into a foam, and the foam is depended into a medical device assembly. The foam hydrates the medical device.

In yet another aspect, a system for making and dosing hydration foam into a medical device assembly includes a supply of hydration liquid, a supply of gas, and a homogenizer in communication with the supply of hydration liquid and the supply of gas, wherein the homogenizer is configured to mix the hydration liquid and gas and to form a foam from the hydration liquid and gas. The system includes a dispensing member configured to dispense the foam into a medical device assembly.

In another aspect, a method of making a urinary catheter product includes placing a hydrophilic catheter within a package, dispensing a first reactant, a second reactant and at least one liquid into the package, and reacting the first reactant with the second reactant to produce a gas that forms a hydration foam with the liquid, wherein the hydration foam hydrates a hydrophilic material of the hydrophilic catheter.

In a further aspect, a packaged urinary catheter includes a package having a sealed cavity. The sealed cavity contains a hydrophilic catheter, a hydration liquid, and a first reactant and a second reactant, wherein when the first and second reactants react, a gas is formed and the gas forms a foam with the hydration liquid.

In yet another aspect, a urinary catheter assembly includes a catheter shaft, a hydrophilic coating on the catheter shaft, wherein the hydrophilic coating is in a hydrated state. The assembly further includes a layer comprising mucilage disposed over the hydrophilic coating.

In another aspect, a device assembly includes a package containing the device, the device including a hydrophilic material, and a hydration medium comprising mucilage located within the package.

In another aspect, a method of making a device assembly includes deploying a hydration medium comprising mucilage into a package containing a catheter, the catheter having a hydrophilic material, and enclosing the catheter within a package.

In yet another aspect, a hydrophilic medical assembly includes a package having a cavity. The cavity contains a hydrophilic medical device including a lubricious hydrophilic material, a hydration fluid, and a deep eutectic liquid.

In another aspect, a hydrophilic urinary catheter assembly includes a package including a cavity. The cavity contains a urinary catheter having a lubricous hydrophilic coating, and a hydration fluid that comprises a deep eutectic liquid.

In another aspect, a hydrophilic urinary catheter assembly includes a package including a cavity. The cavity contains a urinary catheter having a lubricious hydrophilic coating wherein the coating includes a deep eutectic liquid.

In another aspect, a hydrophilic medical device assembly includes a package including a cavity. The cavity contains a hydrophilic medical device, a hydration fluid, and antifreeze protein.

In yet another aspect, a hydrophilic medical device assembly includes a package including a cavity. The cavity contains a hydrophilic medical device, a hydration fluid, and corn syrup.

In another aspect, a hydrophilic medical device assembly includes a package including a cavity. The cavity contains a hydrophilic medical device, a hydration fluid, and a cryoprotectant.

In another aspect, a urinary catheter assembly includes a catheter shaft, a hydrophilic coating on the catheter shaft, and a hydration medium comprising oil disposed over the hydrophilic coating.

In another aspect, a device assembly includes a package containing the device, the device including a hydrophilic material in a hydrated state, and a layer comprising oil disposed over the hydrophilic material.

In yet another aspect, a method of making a device assembly includes applying an oil layer to a hydrophilic material of a catheter, and enclosing the catheter within a package.

In yet another aspect, a hydration fluid or layer includes oil in an amount between 0.01 wt % to 5 wt % of the fluid or layer, water in an amount between 80 wt % to 98.8 wt %, polyol in an amount between 1 wt % to 10 wt %, and surfactant in an amount between 0.01 wt % to 5 wt %.

BRIEF DESCRIPTION OF FIGURES

FIG. 1 is a perspective view of a catheter assembly in accordance with the present disclosure;

FIG. 2 is a perspective view of one embodiment of an insertion aid of the assembly of FIG. 1;

FIG. 3 is a perspective view of another embodiment of an insertion aid of the assembly of FIG. 1;

FIG. 4 is a schematic view of one embodiment of a method of making a hydrophilic sleeved catheter assembly in accordance with the present disclosure;

FIG. 5 is a top plan view of one embodiment of a packaged medical device product containing a medical device and a hydration medium in accordance with the present disclosure;

FIG. 6 is a perspective view of the packaged medical device of FIG. 5 shown with the package in a partially open configuration;

FIG. 7 is a cross-sectional view of the medical device package of FIG. 5;

FIG. 8 is a cross-sectional view of the catheter shaft shown in FIG. 1;

FIG. 9 is a schematic cross-sectional view of the catheter shaft of FIGS. 1 and 8;

FIG. 10 is a schematic cross-sectional view of the catheter shaft of FIGS. 1 and 2;

FIG. 12 is a schematic illustration of another embodiment of a hydration foam forming and dispending system;

FIG. 13 is a schematic illustration of another embodiment of a hydration foam forming and dispending system;

FIG. 15 is a schematic illustration of catheter package receiving solutions during the packaging process, wherein the solutions form a hydration foam;

FIG. 16 is a front plan view of the catheter package of FIG. 15 showing the hydration foam occupying the cavity of the package;

FIG. 17 is a front plan view of another embodiment of a catheter package that includes solutions for forming a hydration foam, wherein one of the solutions in contained in a compartment within the package;

FIG. 18 is a front plan view of the catheter package of FIG. 17, showing compartment being in an opened state;

DETAILED DESCRIPTION OF THE ILLUSTRATED EMBODIMENTS

Figure 11:
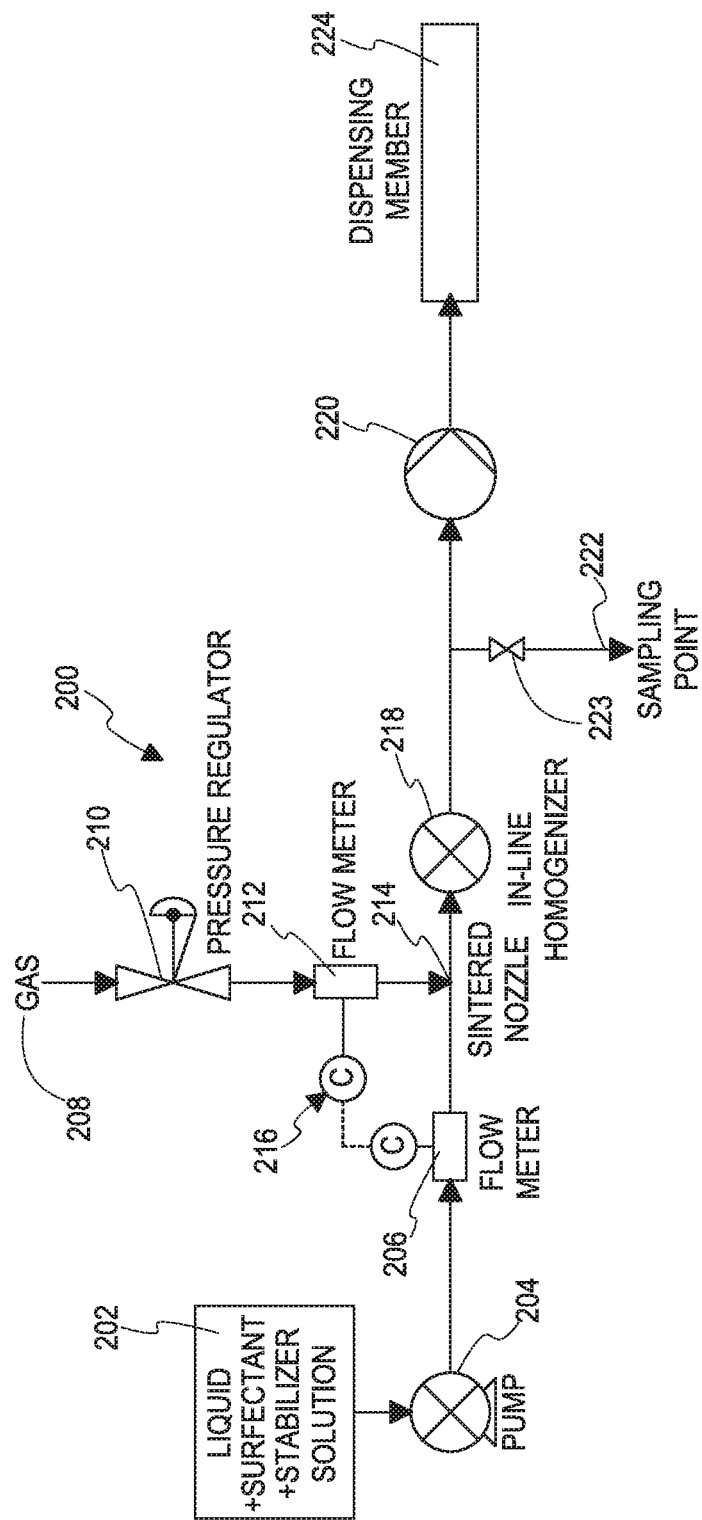
FIG. 11 is a schematic illustration of one embodiment a hydration foam forming and dispensing system.

The embodiments disclosed herein are for the purpose of providing a description of the present subject matter, and it is understood that the subject matter may be embodied in various other forms and combinations not shown in detail. Therefore, specific embodiments and features disclosed herein are not to be interpreted as limiting the subject matter as defined in the accompanying claims.

The present disclosure is directed to hydrophilic medical products that have a package containing a hydrophilic medical device and a hydration medium that hydrates the hydrophilic material of the medical device. The hydrophilic materials may be materials that become lubricious when hydrated, activated or wetted with a hydration medium. The lubricious hydrophilic material may include any suitable hydrophilic polymer such as, polyvinylpyrrolidone, polyethylene oxide, polyurethanes, homo- and copolymers of acrylic and methacrylic acid, polyvinyl alcohol, etc. The hydrophilic material may be a coating on the surface of the medical device. The medical devices may include shafts or tubes that may be inserted into and advanced within a lumen of a body, such as a urethra, anus, esophagus, or fallopian tube. Such medical devices include urinary catheters, fecal catheters, endovascular catheters, endoscopes, exploratory and biopsy devices, etc. While some of the embodiments set forth below may be described in the context of urinary catheters, the disclosure is not limited to such and the features disclosed herein may be applicable to any medical tubing that is inserted into a body lumen.

The present disclosure is also directed to hydration mediums for hydrating medical devices. The hydration medium may be a hydration liquid that includes a liquid, such as water, along with various other components. For example, the hydration medium of the present disclosure includes liquid water and, optionally, one or more of a surface tension reducing agent, mucilage, deep eutectic liquid, oil and osmolality increasing agents. The hydration medium may include other additives and agents as well. Any of the hydration mediums disclosed herein may be used in a foamed or unfoamed state.

Optionally, the hydration medium may be foamed to produce a hydration foam or mousse which may be used to hydrate or wet a device or product. The hydration foam may directly contact the hydrophilic material to hydrate it. The hydration foam includes a mass of gas bubbles formed on or in liquid. Additionally, the creation or formation of the hydration foam may occur at any of the various stages from manufacture to use, depending on the design and use of the medical device. While any of the hydration mediums disclosed herein may be foamed or formed into a foam, depending on the desired use, the hydration mediums disclosed herein also may be employed in an unfoamed state.

Optionally, the hydration medium may include a mucilage. For example, the hydration medium may include water and mucilage, as well as other additives and agents. When a mucilage containing hydration medium is employed, it hydrates the hydrophilic material of the medical device and may form a mucilage layer over the hydrophilic material. For example, when the hydrophilic device is a hydrophilically coated urinary catheter, the hydration medium hydrates the hydrophilic coating and forms a layer containing mucilage over the hydrophilic coating. As will be disclosed in more detail below, the layer of mucilage may have thixotropic properties wherein the layer is thick and viscous under a static condition, and then, becomes less viscous and flows when sheared or otherwise stressed. That is the hydration medium or layer formed therefrom may have a semi-solid or gel-like state and when under stress have more of a liquid state. A hydration medium containing mucilage may be employed in a foamed or unfoamed state.

Optionally, the hydration medium may include a deep eutectic liquid. Deep eutectic liquids can include deep eutectic liquids that are added to the hydration medium and/or and compounds that are added to the hydration medium interact to form a deep eutectic liquid. The hydration medium may include water and a deep eutectic liquid, as well as other additives or agents. Deep eutectic liquids are a mixture or blend of two or more compounds wherein the melting point of the deep eutectic liquid is substantially lower than the melting points of the individual compounds. Deep eutectic liquids have been described as the result of intermolecular hydrogen bonds between the compounds, which at a certain molar ratio leads to a strong depression in the melting point as compared to that of the individual components. Deep eutectic liquids are typically liquid at room temperature (~23° C.). A hydration medium containing a deep eutectic liquid may be employed in a foamed or unfoamed state.

Optionally, the hydration medium may include oil. For example, the hydration medium may include water and oil, as well as other additives and agents. When an oil containing hydration medium is used, it hydrates the hydrophilic material of the medical device and may form a layer containing oil over the hydrophilic material. A hydration medium containing oil may be employed in a foamed or unfoamed state.

Turning now to FIG. 1, this figure illustrates one embodiment of a catheter assembly 10 in accordance with present disclosure, which may be part of a catheter product. The catheter assembly 10 includes an elongated catheter tube 12 having a proximal end portion 14 and a distal end portion 16. The proximal end portion 14 of the catheter tube 12 is suitable for insertion into a lumen or a passageway of the body, such as the urethra. The proximal end portion 14 may include drainage holes or eyelets 18 for draining urine from the bladder. A drainage member 20 may be associated with the distal end portion 16 of the catheter tube 12. The catheter tube 12 includes an outer hydrophilic surface that becomes lubricious when hydrated or activated. The outer surface may be, for example, any suitable hydrophilic coating.

The catheter assembly 10 also includes a sleeve 22, which may be a protective or barrier sleeve, that has a proximal end portion 24 and a distal end portion 26. The sleeve 22 surrounds at least a portion of the catheter tube 12 to separate and enclose the portion of the catheter tube 12 from the outside environment. In other words, the protective sleeve 22 defines an internal cavity in which the catheter tube 12 may be located. In one embodiment, the sleeve 22 extends over the length of the catheter tube 12. Optionally, an insertion aid 28 may be located at the proximal end portion 24 of the sleeve 22. When an insertion aid 28 is present, the proximal end portion 24 of the sleeve 22 may be attached to a barrel 30 of the insertion aid 28, by for example, welding or adhesive. The distal end portion 26 of the sleeve 22 may be attached to the drainage member 20 or the catheter tube 12. An insertion aid may be used with any of the catheter assemblies disclosed herein.

The sleeve 22 may be made of a flexible material which may be vapor permeable or vapor impermeable, depending on the desired use and packaging. The material of the sleeve 22 also may be liquid impermeable or liquid permeable. The sleeve 22 may be formed of any of a variety of thin, flexible polymeric film materials, such as polyethylene, plasticized PVC, or polypropylene, but elastomeric film materials such as polyurethane, and particularly elastomeric hydrogel materials, may be particularly suitable. The thickness of the film from which the sleeve 22 is formed may vary considerably depending on factors such as stretchability and flexibility of the material selected but, in general, the thickness may fall within the range of about 10 to 150 microns, preferably about 13 to 50 microns.

Referring to FIGS. 1, 2 and 3, these figures illustrate exemplary embodiments of the insertion aids. In FIGS. 1 and 2, the insertion aid 28 includes a proximal end portion 32 that defines an introducer tip 34. The introducer tip 34 has a proximal end opening 36 defined by one or more slits between one or more flexible petals 38. The petals 38 may move, bend and/or resiliently deform from the generally closed configuration shown in FIGS. 1 and 2 to an open configuration (not shown) to allow for advancement of the catheter tube 12 therethrough. The distal end portion of the insertion aid 28 includes a cylindrical or barrel portion 30 that has an opening 40 for receiving the catheter tube 12. The insertion aid 28, optionally, also may include an intermediate flange 42 that may contact the user around the urethral opening and act as a stop to limit the insertion of the introducer tip 34.

Turning to FIG. 3, in this embodiment the introducer aid 28a is a port 29a that includes a flange 42a surrounding an opening 34a. The catheter tube 12 advances through opening 34a for insertion into the urethra. The distal end portion of the port 29a includes a cylindrical or barrel portion 30a that has an opening 40a for receiving the catheter tube 12.

Turning back to FIG. 1, the introducer aid 28, optionally, may be covered by a removable protective cap 44. The removable protective cap 44 covers the introducer aid 28 and may protect the introducer aid 28 from contacting surfaces and objects prior to use.

To use the catheter assembly 10, the user opens and removes the catheter assembly 10 from an outer package, which may be similar to the package shown in FIGS. 5 and 6. For example, the user opens the package and grasps the catheter tube 12 through the protective sleeve 22 to handle and manipulate the catheter assembly 10. The user removes protective cap 44, if one is present. If the catheter assembly 10 includes the optional insertion aid 28 shown in FIG. 2, then the user inserts the introducer tip 34 into the urethra. If the catheter assembly 10 includes the optional insertion aid 28a shown in FIG. 3, then the user aligns the opening 34a of the port 29a with the urethral opening. The user then grasps the catheter tube 12 through the sleeve 22 and advances the catheter tube 12 through the introducer aid 28/28a, if present, and into and through the urethra until the eyelets enter the bladder. If the catheter assembly 10 does not includes an insertion aid, then the user grasps the catheter tube 12 through the sleeve 22 and advances the tip of the catheter tube 12 out of the open end of the sleeve 22 and into the urethra. When the eyelets enter the bladder, urine flows through the eyelets and catheter tube 12 to drain the bladder.

In one method of making a sleeved hydrophilic catheter wherein the hydrophilic surface is in an activated or hydrated state, such as those described above, the method includes delivering a hydration medium into the internal cavity of the sleeve of the catheter assembly. While in the sleeve, the hydration medium contacts the hydrophilic surface of the catheter to at least partially hydrate or activate the hydrophilic surface. The hydration medium may be any of the hydration mediums discussed herein. The hydration medium may be a foamed hydration medium or an unfoamed hydration medium. When a foamed hydration medium is employed, the foam may be configured so that after a period of time, the foam will coalesce and collapse (bubbles break or dissipate) and the volume of the foam will decrease or the hydration medium will become unfoamed. Optionally, the foamed hydration medium may be configured as to not coalesce. Furthermore, the foamed hydration medium may be such that a coalesced hydration medium refoams from agitation, such as by shaking the catheter product.

Turning now to FIG. 4, this figure provides a schematic representation of a method that includes an injection system 52 for injecting a hydration medium into the sleeve of a catheter assembly 10. The catheter assembly 10 may be docked or otherwise operatively connected to a hydration medium delivery system or machine 52. The delivery system 52 may include a source of hydration medium 56, which could be a reservoir or tank 54 containing an amount of hydration medium 56. The system may include a conduit 58 one end 60 of which is connected to the source of hydration medium 56 and the end 62 of which is configured to be connected to the catheter assembly 10 so that hydration medium 56 can be delivered into and the interior cavity of the sleeve 22. For example, the end 62 of the conduit 58 may include a nozzle 64 configured to be releasably connectable to the sleeve 22 or the introducer aid 28, if one is present. The system also includes a pump or metering valves or other element 66 for moving/pumping hydration medium 56 so as to inject hydration medium into the sleeve 22.

As discussed above, the method of forming the sleeved activated hydrophilic catheter may include injecting a hydration medium into the interior cavity of the sleeve, wherein the hydration medium comes into contact with the outer hydrophilic surface of the catheter tube. When the hydration medium is a foam medium, foam may also serve as a visual indicator by human or electronic eye to confirm that the hydration medium has been injected into the sleeve. After the hydration medium 56 has been injected, the nozzle 64 is undocked and the protective cap 44, if one is present, is placed on or refitted onto the insertion aid 28. The catheter assembly 10 is then placed within a package (such as a package shown in FIGS. 5 and 6) and the package is sealed. The package may then be submitted to sterilization by e-beam or gamma radiation.

In one embodiment, the package may be made of a gas impermeable and liquid impermeable material, such as a polymer and aluminum laminate. Furthermore, the package may be of the type that has a vapor atmosphere or 100% relative humidity within the seal package. For example, the package may include therein a water compartment that is at least partial defined by a vapor permeable, liquid impermeable material. The water within the compartment may produce a water vapor that permeates through the vapor permeable, liquid impermeable material to create and/or maintain a hydration environment within the package. Additionally, when the catheter assembly is placed in a package having a vapor atmosphere, the sleeve may be vapor permeable to allow vapor to come into contact with the partially or substantially hydrated hydrophilic surface of the catheter tube. This may assist in maintaining the hydrophilic surface in an activated or hydrated state during storage and distribution.

In another embodiment, the sleeve may be liquid permeable such that liquid outside of the sleeve permeates through the sleeve to hydrate the hydrophilic medical device. In such an embodiment, the hydration medium, such as a form hydration medium, may be placed in the package outside of the sleeve. The hydration medium migrates through the sleeve and hydrates the hydrophilic medical device.

Turning now to FIGS. 5-7, these figures illustrate a medical device package 100 for containing a medical device 112, such as the illustrated catheter, and a hydration medium 130 (FIG. 7). The package, optionally, could also contain a gripping aid, such as a tubular gripper positioned around the catheter shaft. Optionally, in any of the catheters disclose herein, the distal end of the catheter may be connected to a collection bag. In such embodiment, the collection bag may be contained in the package with the catheter. The hydration medium may be any of the hydration mediums disclosed herein, and the hydration medium may be in a foamed or unfoamed state. The medical device may be any suitable medical device. In the illustrated embodiment, the medical device is a hydrophilic catheter.

The package 100 may be any suitable package for holding the device. For example, the package may be a tear open package, such as a side tear open package, or a peel open package. In the illustrated embodiment, the package 100 includes a front sheet 114 and a back sheet 115 (FIGS. 6 and 7). The front sheet 114 includes an inner surface 116 facing the back sheet 115, an outer surface 117 facing the ambient atmosphere, a top edge 118, bottom edge 119 and opposed first and second side edges 120 and 121. Referring to FIGS. 6 and 7, the back sheet 115 includes an inner surface 122 facing the front sheet 114, an outer surface 128 facing the ambient atmosphere, a top edge 123, bottom edge (not shown) and opposed first and second side edges 124 and 125.

The front sheet 114 and back sheet 115 may be made from a liquid and gas impermeable material. For example, the front and back sheets 114 and 115 may be made from a polymer film and/or a metal film. In one embodiment, the material may be a polymer/metal laminate, such as a polymer/aluminum laminate.

The front sheet 114 and back sheet 115 may be sealed to each other to define a cavity for holding the catheter 112. In one embodiment, the front sheet 114 and back sheet 115 may be sealed to each other to form a gas tight cavity. In the illustrated embodiment, the front sheet 114 and back sheet 115 are sealed to each other by a peripheral seal 126. The peripheral seal 126 may be a peelable seal that may be a heat seal, an adhesive seal or any other suitable peelable seal that allows the front sheet 114 to be separated from the back sheet 115 when the sheets are peeled apart during use. As illustrated in FIG. 7, the package 100 may include the hydration foam 130 and the device 12.

Turning now to the hydration mediums that may be used in a medical device product to hydrate the medical device. As mentioned above, the hydration medium may include water and mucilage. Optionally, the hydration medium may include other additives and agents, such as a polyols, surface tension reducing agents, osmolality increasing agents and deep eutectic liquids. The hydration medium hydrates the hydrophilic coating of the medical device, such as a hydrophilic coating of a catheter. The hydration medium also may form a mucilage containing layer over the hydrophilic coating. The mucilage containing layer assists in enhancing the performance of the medical device. For example, the mucilage containing layer may hydrate the hydrophilic material, protect the hydrophilic material during radiation sterilization, increase lubriciousness, reduce dry-out of the hydrophilic material, increase the time period for which the hydrophilic material is lubricious, etc.

The hydrophilic medical device may be contained in a package wherein the mucilage containing layer is a distinct layer that is in contact with a surface of the hydrophilic material. The hydration medium and mucilage containing layer may have thixotropic properties wherein the medium/layer is thick and viscous under a static condition, and then, becomes less viscous and flows when sheared or otherwise stressed. During delivery of the hydration medium to hydrate the hydrophilic material of the medical device, the hydration medium is under stress and, optionally foamed, which results in the hydration medium being less viscous and in a more liquid or liquid-like state. In this less viscous state, the medium flows over and covers the hydrophilic material. After the hydration medium has been delivered, the hydration medium is under a relatively more static condition. Under the static condition, the hydration medium forms a layer including mucilage disposed over the hydrophilic material. When the medium is foamed, the layer may form as the foam coalesces and collapses. During catheterization, the mucilage containing layer is placed under shear or other stress, and the hydration medium/layer becomes less viscous and flows easier. For example, when the catheter is inserted into a urethra, the hydration medium/layer is placed under shear stress and the hydration medium/layer becomes less viscous and flows.

This thixotropic property of the medium/layer provides a hydration medium/layer that has an anti-gravity effect in that the layer tends to remain in place on the surface of the hydrophilic material of the device, when it is in a static condition, regardless of the device's orientation. Thus, the layer tends to remain over and hydrate the hydrophilic material of the device regardless of the orientation of the device during storage. This allows the device to be stored in any orientation, e.g. vertical, horizontal, etc. This assists in maintaining uniform hydration of the hydrophilic material during storage, which assists in the device being ready to use right out of the package.

Turning to FIGS. 8 and 9, a mucilage containing layer 132 formed from the hydration medium may be disposed over the hydrophilic coating 134, which is one a catheter tube 136. The hydrophilic coating 134 may have been pre-hydrated with a hydration medium, such as water or saline. Pre-hydration may include exposing the hydrophilic coating 134 to hydration medium by dipping, spaying or immersing the hydrophilic coating 134 in liquid water or saline. In another embodiment, the hydrophilic coating 134 may be hydrated by the mucilage containing layer 132 after hydration medium has been disposed over the coating. The mucilage containing layer 132 may be disposed over the hydrophilic coating 134, by dipping or immersing the hydrophilic coating 134 in a bath of water and mucilage. In another embodiment, hydration medium containing mucilage may be placed in the package 120 with the catheter 112 (FIG. 5) or may be placed into the sleeve 22 containing the catheter shaft 12 (FIG. 1). As mentioned above, the hydrophilic coating 134 may be pre-hydrated and/or may be hydrated by the mucilage containing layer 132.

It should be understood that the mucilage containing hydration medium forms a layer on the hydrophilic device. As such, the mucilage containing hydration medium and the layer include the same or similar components. The mucilage in the mucilage containing hydration medium/layer 22 may include one or more exopolysaccharide. They may also include a polar glycoprotein. The mucilage of the hydration medium/layer 22 may be derived from one or more of *Aloe vera*, *Basella alba*, cactus, *Chondrus crispus*, *Corchorus*, *Dioscorea polystachya*, Chinese yam, *Drosera*, *Drosophyllum lusitanicum*, flax seeds, kelp, liquorice root, marshmallow, mallow, mullein, okra, *Parthenium*, *Pinguicula*, *Psyllium* seed, *Salvia hispanica* seed, *Talinum triangulare*, *Ulmus rubra* bark, and *Plantago major*.

Furthermore, the mucilage may contain an exopolysaccharide that is derived from bacteria. The exopolysaccharides may include, but are not limited to one or more of acetan, alginate, cellulose, chitosan, curdlan, cycloso-phorans, dextran, emulsan, galactoglucopolysaccharides, galactosaminogalactan, gellan, glucuronan, N-acetylglucosamine, N-acetyl-heparosan, hyaluronic acid, indicant, kefiran, lentinan, levan, pullulan, scleroglucan, schizophyllan, stewartan, succinoglycan, xanthan, welan or derivatives thereof.

The mucilage containing hydration medium/layer may include other compositions, additives or agents. Optionally, the mucilage containing hydration medium/layer may include water, saline, and/or oil. The oil may include but is not limited to vegetable oil, such as rapeseed oil, olive oil, sunflower oil, mustard oil, vegetable oil etc. Optionally, the mucilage containing hydration medium/layer may also include a polyol. The polyols include but are not limited to one or more of glycerol and polyethylene glycol. In one embodiment, the mucilage containing hydration medium/layer includes glycerol.

Optionally, the mucilage containing hydration medium/layer may further include a surface tension reducing agent, such as a surfactant. When the hydration medium is foamed, the surface tension reducing agent may assist in the foaming of the hydration medium. Surfactants include, but are not limited to, one or more of saponified coconut oil, vitamin E, polyoxyethylene sorbitan monolaurate, sodium dodecyl sulfate, tween 20, tween 80, polysorbate, L-α-phosphatidylcholine, lecithin, stearyl stearate, sodium stearate, sodium laurate, sodium myristate, sodium myristate, sodium palmitate, sodium oleate, polyethylene glycol monododecyl ether, glycolic acid ethoxylate lauryl ether, glycolic acid ethoxylate oleyl ether, ethylene glycol monododecyl ether, polyoxyethylene glycerol ester, polyglyceryl esters, diglyceryl diisostearate, diglyceryl monolaurate, diglyceryl monooleate, Docusate sodium, dioctyl sulfosuccinate sodium salt, dioctyl sodium sulfosuccinate, sodium dodecylbenzenesulfonate, perfluorobutane sulfonic acid, 3-sulfopropyl ethoxylate lau-rylphenly ether, lauric acid sodium salt, N-acylsarcosine sodium salt, N-lauroylsarcosine sodium salt. When the mucilage containing hydration medium is foamed, the mucilage may serve as a foam stabilizer that slows coalescence of the foam.

In one embodiment, the mucilage containing hydration medium/layer may contain about 0.01 wt % to about 10 wt % mucilage, with the balance being water and, optionally, other additives and agents. The mucilage could be at least about 5 wt % of the hydration medium/layer. In another embodiment the mucilage is less than about 0.5 wt % of the hydration medium/layer. As mentioned above, the mucilage containing hydration medium/layer may include other components as well. Optionally, the mucilage containing hydration medium/layer could include about 90 wt % to about 99.9 wt % water. The water could be at least about 95 wt % of the hydration medium/layer. In another embodiment, the water could be less than about 99.5 wt %. Optionally, the mucilage containing hydration medium/layer could include oil at between about 0.05 wt % and about 5 wt %. The oil could be at least about 1 wt % of the medium/layer. In another embodiment the oil could be less than about 0.2 wt %. Optionally, the mucilage containing hydration medium/layer could include about 0.1 wt % to about 9.2 wt % polyol. The polyol could be at least about 4.6 wt % of the medium/layer. In another embodiment, the polyol could be less than about 1 wt %. Optionally, the mucilage containing hydration medium/layer could include about 0.05 wt % to about 2 wt % of a surfactant. The surfactant could be at least about 0.5 wt % of the medium/layer. In another embodiment the surfactant could be less than about 0.1 wt %.

In one exemplary embodiment, the mucilage containing hydration medium/layer could include:

| | |
|---|---|
| Mucilage | 1.1 wt % to 5.1 wt % |
| Water | 98.5 wt % to 94.9 wt % |
| Polyol | 1 wt % to 4.6 wt % |
| Surfactant | 0.1 wt % to 0.5 wt % |

In one embodiment, the mucilage containing hydration medium/layer may include xanthan gum in an amount between about 0.1 wt % and about 1 wt %, optionally, a surfactant (such as Sodium Methyl Cocoyl Taurate) in an amount between about 0.05 wt % and about 0.2 wt %, optionally, oil in an amount of between about 0.05 wt % and about 1 wt % and the balance a solution of water and glycerol, wherein the water is at 98 wt % of the solution and the glycerol is 1 wt % of the solution. It will be understood that the water and glycerol could be added to the hydration medium/layer separately, at the same ratio, and not as a solution. The hydration medium/layer could include other components as well, such as antimicrobial, fragrances, epithelial medicates, etc. Optionally, the mucilage containing hydration medium/layer could also include an osmolality increasing agent and/or a deep eutectic liquid, such as any of those discussed below. Optionally, the polyol could serve as an osmolality increasing agent.

Referring to FIG. 9, the hydrophilic coating 134 is deposed on a catheter shaft 136. The mucilage containing hydration medium/layer 132 is formed from exopolysaccharide molecules 140 and water droplets 142. Optionally, the hydration medium/layer may include oil droplets 144 and a surfactant (not shown). The mucilage containing hydration medium/layer 132 may trap water droplets 146 and provide an ample supply of water molecules to hydrate, maintain and/or supplement the hydration of hydrophilic coating 134.

As mentioned above, the mucilage containing hydration medium/layer 132 may exhibit thixotropic properties wherein it is in a semi-solid phase on which any applied shear force turns the mucilage containing layer into a more liquid phase. The mucilage layer has lose structure of exopolysaccharide molecules and water droplets, and optionally, oil droplets and surfactant molecules, held together by weak forces (e.g. Van Der Waal forces)—exhibiting a liquid—semi solid structure and enhancing coating lubricity performance, which aids in lubricity of the coating 134. Additionally, the mucilage containing hydration medium/layer 132 may assist in immobilizing a water layer onto the hydrophilic coating 134 and trapping water droplets 146. The mucilage containing hydration medium/layer 132 also may exhibit a semisolid phase which upon shearing becomes liquid.

In one embodiment the mucilage containing hydration medium/layer is formed by mixing polyol and water mixture for 30 minutes at 100 rpm agitation. Then mucilage ingredients are added into polyol and water solution and homogenized at 500-10,000 rpm for 5 to 30 minutes to attain homogeneous solution. Alternatively, exopolysaccharide can be mixed at slow agitation of 100 rpm with polyol and water solution which is heated to 40-75° C. for 30 to 120 minutes. Optionally, oil may be added and homogenized at 500-10,000 rpm to form stable emulsion. Optionally, surfactant is added to homogeneous mucilage solution with or without oil and mixed at low agitating speed of 50-100 rpm for 5-15 minutes. Optionally, a deep eutectic liquid may be added to the solution. This homogeneous solution of the hydration medium/layer may be formed into a foam or can be used in an unfoamed state.

The mucilage containing hydration medium/layer may be applied over/disposed on the coating by injecting mucilage containing solution or foam into the sleeve or other container surrounding a catheter or into the package containing the catheter.

The hydrophilic medical device products may also include a hydrophilic medical device and oil containing hydration medium or layer disposed over the hydrophilic materials of the device. For example, the separate layer may formed from a hydration medium contains oil, wherein the oil comprises or is an oil emulsion. As discussed in more detail below, the hydrophilic materials may be a hydrophilic coating on the surface of the medical device and the oil containing hydration medium/layer, which is separated from the hydrophilic coating, may be disposed over, disposed on and/or superimposed over the hydrophilic coating.

The oil containing hydration medium/layer may enhance the performance of the medical device. For example, the oil containing hydration medium/layer may hydrate the hydrophilic material, protect the hydrophilic material during radiation sterilization, increase lubriciousness, reduce dryout of the hydrophilic material, increase the time period for which the hydrophilic material is lubricious, etc.

The oil containing hydration medium/layer may include a hydration liquid that may be any hydration liquid that hydrates, activates or wets the hydrophilic material thereby rendering it lubricious. They hydration liquid may be liquid water or saline.

Turning to FIG. 10, an oil containing hydration medium/layer 150 may be disposed over the hydrophilic coating 134, which is on a catheter shaft 136. The hydrophilic coating 134 may have been pre-hydrated with a hydration liquid, such as water or saline. Pre-hydration may include exposing the hydrophilic coating 134 to hydration liquid by dipping, spraying or immersing the hydrophilic coating 134 in liquid water or saline. In another embodiment, the hydrophilic coating 134 may be hydrated by the oil containing hydration medium/layer 150 after layer 150 is disposed over the coating. The oil containing hydration medium/layer 150 may be disposed over the hydrophilic coating 134, by dipping or immersing the hydrophilic coating 134 in a bath of a hydration liquid including oil, wherein the oil has formed an oil emulsion. In another embodiment, a hydration liquid containing oil may be placed in the package with the catheter (FIG. 5) or may be placed into the sleeve containing the catheter shaft (FIG. 1). As mentioned above, the hydrophilic coating 134 may be pre-hydrated and/or may be hydrated by the oil containing layer.

The oil in the oil containing hydration medium/layer 150 may include one or more essential oils, such as tocopherol, menthol, thymol, carvacrol etc. The oil also may be a vegetable oil, such as rapeseed oil, olive oil, sunflower oil, mustard oil, etc. The oil also may be selected to provide a fragrance and/or to provide a therapeutic effect or a sensation. Oils included in any of the hydration mediums disclosed herein may serve to provide a fragrance and/or to provide a therapeutic effect or a sensation. For example, oil may be provided to add a fruity scent, such a lemon or strawberry scent, that the user experiences when the package is opened.

The oil containing hydration medium/layer may include other compositions, additives or agents. For example, the oil containing hydration medium/layer may include a polyol, such as one or more of glycerol and polyethylene glycol. In one embodiment, the oil containing hydration medium/layer includes glycerol. The oil containing layer may further include any of the above-mentioned surface tension reducing agents, such as a surfactant.

In one embodiment, the oil containing hydration medium/layer may contain about 0.01 wt % to about 5 wt % oil, with the balance being water and, optionally, other additives. The oil could be at least about 0.01 wt % of the hydration medium/layer. In another embodiment the oil is less than about 5 wt % of the hydration medium/layer. As mentioned above, the hydration medium/layer may include other components as well. Optionally, the hydration medium/layer could include about 80 wt % to about 99.9 wt % water. The water could be at least about 80 wt % of the hydration medium/layer. In another embodiment the water could be less than about 99.9 wt %. Optionally, the hydration medium/layer could include about 0.1 wt % to about 10 wt % polyol. The polyol could be at least about 0.01 wt % of the hydration medium/layer. In another embodiment the polyol could be less than about 1 wt %. Optionally, the hydration medium/layer could include about 1 wt % to about 5 wt % of a surfactant. The surfactant could be at least about 1 wt % of the hydration medium/layer. In another embodiment the surfactant could be less than about 5 wt %.

In one exemplary embodiment, the hydration medium/layer could include:

| | |
|---|---|
| Oil | 0.01 wt % to 5 wt % |
| Water | 80 wt % to 98.8 wt % |
| Polyol (optionally) | 1 wt % to 10 wt % |
| Surfactant (optionally) | 0.01 wt % to 5 wt % |

In one embodiment, the hydration medium/layer may include an essential oil or a vegetable oil in an amount between about 0.01 wt % and about 5 wt %, a surfactant, such as Sodium Methyl Cocoyl Taurate, in an amount between about 0.01 wt % and about 5 wt %, and the balance a solution of water and glycerol. In one embodiment, the water is between about 89 wt % and 98.8 wt % of the solution and the glycerol is 1 wt % of the solution. It will be understood that the water and glycerol could be added to the hydration liquid/layer separately, at the same ratio, and not as a solution. The layer could include other components as well, such as antimicrobial, fragrances, epithelial medicates, etc.

Turning back to FIG. 10, the hydrophilic coating 134 is deposed on a catheter shaft 136. The layer 150 is formed from the hydration liquid which includes water droplets 152, oil droplets 154, and surfactant 156. The oil and surfactant produces an emulsion. The rate of homogenization will determine the size of oil droplets and smaller the droplet size more stable is the emulsion coupled with surfactant composition. The oil containing layer 150 may trap water droplets 158 and provide an ample supply of water molecules to hydrate, maintain and/or supplement the hydration of hydrophilic coating 134. In one embodiment the size of the oil droplets may be between about <1 µm and about 100 µm. In another embodiment the size of the oil droplets may be at most <1 µm to 10 µm.

The oil containing hydration medium may be applied over/disposed on the coating by injecting the oil containing solution into a pack containing a catheter or into a sleeve or other container surrounding a catheter. The hydration medium forms a layer over the hydrophilic coating.

As mentioned above, the hydration medium, optionally, may include a deep eutectic liquid. The deep eutectic liquid could also be included in the hydrophilic coating and/or the formulation that forms the hydrophilic coating.

Deep eutectic liquids are a mixture or blend of two or more compounds wherein the melting point of the deep eutectic liquid is substantially lower than the melting points of the individual compounds. Deep eutectic liquids have been described as the result of intermolecular hydrogen bonds between the compounds, which at a certain molar ratio leads to a strong depression in the melting point as compared to that of the individual components. Deep eutectic liquids are typically liquid at room temperature (~23° C.).

The components of deep eutectic liquids may include salts, sugars, sugar alcohols, polyols, organic acids, amino acids, and amines. The deep eutectic liquids may be natural or synthetic. In one deep eutectic liquid, the liquid includes a halide salt and a hydrogen bond donor. The halide salt may be, for example, one or more of quaternary ammonium halide salt, choline chloride, acetylcholine chloride, betaine, tetrabutylammonium chloride, and 2-(diethylamino)ethanol chloride. The hydrogen bond donor may be one or more alcohols, carboxylic acid, sugar, polyol, amines and amides. For example, the hydrogen bond donor may be one or more of urea, 1,3-dimethylurea, methylurea, glycerol, trehalose, mannose, ethylene glycol, D-xylose, D-glucose, oxalic acid, succinic acid and citric acid. In one embodiment, the deep eutectic liquid may include choline chloride and urea. The molar ratio of choline chloride to urea may be about 1:2.

In another embodiment, the deep eutectic liquid may include a sugar and a polyol. For example, the sugar may be mannose or trehalose and the polyol may be glycerol. The deep eutectic liquid may be for example trehalose and glycerol at a molar ratio between about 1:30 to about 1:550 molar ratio. In one embodiment the molar ratio is 1:30. When used in hydration medium or in a hydrophilic coating, which may contain other components, the molar ratio between the components trehalose and glycerol in the medium or the coating may be about 1:30 to about 1:550, including all of the ratios therebetween. In one embodiment the molar ratio is 1:30, and in another embodiment the ratio is greater than 1:30. In other embodiments, the molar ratio of these components is about 1:20 to about 1:1000. In yet another embodiment the molar ratio is about 1:30 to about 1:550. In another embodiment, the molar ratio may be 1:100 or greater.

The deep eutectic liquid may be contained in the hydrophilic material and/or in the hydration medium. The deep eutectic liquid may enhance the performance of the catheter. For example, the deep eutectic liquid, whether in the coating or the in the hydration medium, may enhance the lubricity of the hydrophilic material, may result in a smoother texture on the surface of the hydrophilic coating and/or may reduce the risk of damage to the catheter coating due to exposure to temperature and/or climate change.

Regarding a smoother feeling texture on the surface of the hydrophilic coating. Urinary catheters are inserted and advanced through the urethra of the user to drain the bladder. During advancement and withdrawal of the urinary catheter, the outer surface of the hydrophilic material contacts and slides against the wall of the urethra. Having a smoother surface texture may reduce the risk of irritation to the urethral wall. Additionally, because the catheter is being inserted into an intimate part of the body, some users may feel more comfortable with inserting a catheter having a smoother surface or texture than rougher one.

Regarding exposure to temperature changes, users of intermittent urinary catheters can self-catheterized around six times a day or more. Because of this, catheter users usually carry a supply of catheters with them. In colder climates, the catheters may be exposed to temperatures below freezing. In some instances, exposure to colder temperatures may increase the risk of damage to the hydrophilic coating of the catheter. The addition of deep eutectic liquids to the catheter assembly may serve as a cryoprotectant that reduces the risk of damage to the catheter when exposed to cold temperatures.

As mentioned above, a urinary catheter may have a hydrophilic coating wherein the deep eutectic liquid is incorporated or impregnated in the hydrophilic coating. For example, a hydrophilic coating may include polyvinylpyrrolidone and the deep eutectic liquid, such as a deep eutectic liquid including trehalose and glycerol. The deep eutectic liquid may be included in the hydrophilic coating formulation that is used to form the hydrophilic coating. Alternatively, the hydrophilic coating may be formed and then impregnated with the deep eutectic liquid by, for example, immersion of the coating into the deep eutectic liquid or a solution containing the deep eutectic liquid. The amount of the deep eutectic liquid in the hydrophilic coating may be 0.1 wt %-15 wt % by weight. In other embodiments the deep eutectic liquid may be more than 15 wt %. In one embodiment, the deep eutectic liquid in the hydrophilic coating may be a trehalose:glycerol complex at any of the above discussed molar ratios. In one embodiment, the trehalose: glycerol complex may be between about 8 wt % and 12 wt % of the coating. In addition to the deep eutectic liquid, the hydrophilic coating may include other agents or additives as well. Incorporating the deep eutectic liquid within the hydrophilic coating may be useful in the situation wherein the hydration medium is a liquid or a vapor and the hydrophilic coating is vapor or liquid hydrated.

As also mentioned above, the hydration medium may contain a deep eutectic liquid. In one embodiment, the hydration medium may include liquid water and a deep eutectic liquid. The hydration medium may include other additives and agents, as well. The amount of liquid water in the hydration medium may be at least about 75 wt %. In one embodiment, the amount of water may be between about 75 wt % and about 99 wt %. The amount of deep eutectic liquid in the hydration medium may be about at least 1 wt %. In one embodiment, the amount of deep eutectic liquid may be between about 1 wt % and about 20 wt %. For example, the hydration medium may include about 80 wt % to about 99 wt % liquid water and about 1 wt % to about 20 wt % deep eutectic liquid, such as trehalose/glycerol at any of the above discussed molar ratios. The hydration medium may include other agents and additives as well.

In one embodiment, the hydration medium may be made by combining 95.4 wt % of water, 0.15 wt % Trehalose dehydrate, 1.095 wt % of Glycerol and adding 3.355 wt % of Glycerol. In another embodiment, the hydration medium may be made by combining 95.4 wt % water, 1.254 wt % Trehalose:Glycerol (at 1:30 molar ratio) and adding 3.355 wt % Glycerol. In yet another embodiment, the hydration medium may be made by combining 95.4 wt % of water, 0.55 wt % Trehalose dehydrate and adding 4.05 wt % of Glycerol. The hydration medium may include other agents or additives as well. For example, the hydration medium, optionally, may also include any the above disclosed surface tension reducing agents. When the hydration medium is a foamed hydration medium, the surface tension reducing agents may assist in foaming the hydration medium. The hydration medium, optionally, may also include mucilage.

Optionally, the hydrophilic medical device assembly may include an antifreeze protein (AFP). The antifreeze protein may be incorporated into the hydrophilic material and/or may be incorporated into any of the hydration mediums disclosed herein. Antifreeze proteins, sometimes referred to as ice binding proteins, are ice-restructuring protein compounds that have an affinity for ice. It is believed that antifreeze proteins disrupt hydrogen bonding during the formation and/or buildup of ice crystals, thereby preventing formation and/or buildup of larger ice crystals. When an ice front is in equilibrium with a solution, slight undercooling of the solution below the equilibrium freezing point allows water molecules to join the ice lattice. Consequently, the ice front will advance. Generally, solutes including the vast majority of proteins (such as bovine serum albumin and myoglobin) will be excluded and pushed ahead of the growing ice front. Anti-freeze proteins behave differently since they are adsorbed into the ice (Raymond & DeVries 1977). The entrained AFPs restrict the growth of the ice front to regions between the adsorbed protein molecules.

The antifreeze proteins may include antifreeze glyco proteins (AFGP), which display many disordered saccharide OH groups. Additionally, the antifreeze protein may be natural or synthetic. The antifreeze protein may be derived from one or more of an animal, plant, insect and microorganism.

The medical device assembly may include antifreeze proteins as a cryoprotectant to reduce the risk of damage to the catheter when the catheter is exposed to cold temperatures.

In one embodiment, the antifreeze protein may include protein compounds having a sugar group attached thereto. The protein may include threonine, alanine, serine, lysine, asparagine, leucine, valine and/or other amino acids. Suitable antifreeze proteins include, but are not limited to, AFGP, AFP Type I, AFP Type II, AFP Type III, AFP Type IV, and/or other natural or synthetic antifreeze proteins.

As mentioned above, a urinary catheter may have a hydrophilic coating wherein the antifreeze proteins are incorporated or impregnated in the hydrophilic coating. For example, a hydrophilic coating may include polyvinylpyrrolidone and the antifreeze proteins. The antifreeze proteins may be included in the hydrophilic coating formulation that is used to form the hydrophilic coating. The amount of the antifreeze proteins in the hydrophilic coating formulation may be about 0.05 wt % to about 2.0 wt %. Alternatively, the hydrophilic coating may be formed and then impregnated with the antifreeze proteins by, for example, immersion of the coating into a solution that includes antifreeze proteins. In addition to the antifreeze proteins, the hydrophilic coating may include other agents or additives as well. Incorporating the antifreeze proteins within the hydrophilic coating may be useful in the situation wherein the hydration medium is water vapor and the hydrophilic coating is vapor hydrated.

As also mentioned above, the hydration medium may contain antifreeze proteins. In one embodiment, the hydration medium may include liquid water and antifreeze proteins. The hydration medium may include other additives and agents, as well. The amount of liquid water in the hydration medium may be at least about 90 wt %. In one embodiment, the amount of liquid water may be between about 95 wt % and about 99.9 wt %. The amount of antifreeze proteins in the hydration medium may be about at least 0.1 wt %. In one embodiment, the amount of antifreeze proteins may be between about 0.1 wt % and about 10 wt %. For example, the hydration medium may include about 95 wt % to about 99.9 wt % water and about 5 wt % to about 0.1 wt % antifreeze proteins. The hydration medium may include other agents or additives as well. For example, the hydration medium, optionally, may also include any the above disclosed surface tension reducing agents. When the hydration medium is a foamed hydration medium, the surface tension reducing agents may assist in foaming the hydration medium. The hydration medium, optionally, may also include mucilage.

In yet another embodiment of a hydrophilic medical device assembly, the assembly may include a package including a cavity, wherein the cavity contains a hydrophilic medical device, a hydration medium, and corn syrup. The corn syrup may be incorporated into the hydrophilic coating and/or any of the hydration mediums disclosed herein.

For example, a hydrophilic coating may include polyvinylpyrrolidone and the corn syrup. The corn syrup may be included in the hydrophilic coating formulation that is used to form the hydrophilic coating. The amount of the corn syrup in the hydrophilic coating formulation may be about 0.2 wt % to about 2 wt %. Alternatively, the hydrophilic coating may be formed and then impregnated with corn syrup by, for example, immersion of the coating into a solution that includes corn syrup. In addition to the corn syrup, the hydrophilic coating may include other agents or additives as well. Incorporating the corn syrup within the hydrophilic coating may be useful in the situation wherein the hydration medium is a vapor and the hydrophilic coating is vapor hydrated.

As also mentioned above, the hydration medium may contain corn syrup. In one embodiment, the hydration medium may include liquid water and corn syrup. The hydration medium may include other additives and agents, as well. The amount of water in the hydration medium may be at least about 90 wt %. In one embodiment, the amount of water may be between about 95 wt % and about 99.5 wt %. The amount of corn syrup in the hydration medium may be about at least 0.5 wt %. In one embodiment, the amount of corn syrup may be between about 0.5 wt % and about 10 wt %. For example, the hydration medium may include about 95 wt % to about 99.8 wt % water and about 5 wt % to about 0.2 wt % corn syrup. The hydration medium may include other agents or additives as well. For example, the hydration medium, optionally, may also include any the above disclosed surface tension reducing agents. When the hydration medium is a foamed hydration medium, the surface tension reducing agents may assist in foaming the hydration medium. The hydration medium, optionally, may also include mucilage.

Hydration Foam

As discussed above, any of the hydration mediums disclosed herein may be employed in a foamed or unfoamed state. When the hydration medium is foamed or employed as a hydration foam, the foam includes gas bubbles on or in a liquid. The hydration medium may be foamed or formed into a foam in any suitable manner. For example, the foam may be formed by homogenizers, mixtures or agitators. The foam also could be foamed by aerosol and/or chemical reaction. The foam also could be formed by physical shaking of the medical product/package. For example, the end user could shake the package to form the hydration liquid into a hydration foam. Furthermore, the creation or formation of the hydration foam may occur at any of the various stages from manufacture to use, depending on the design and use of the medical device.

The hydration foam may include a hydration liquid and a mass of bubbles formed on or in the hydration liquid. The bubbles may be formed from any various gases, and in one embodiment, the bubbles are formed from ambient air. The bubbles may have an average size between 1 μm and 100 μm. In one embodiment the average bubble size is less than 1 μm. Optionally, the hydration liquid to gas ratio is about 1 to 7 to about 4 to 7 by volume.

The hydration liquid may be water, an aqueous solution or other suitable liquid or solution. When the hydration liquid includes water or an aqueous solution, the water may be de-ionized. The hydration foam may be formed by any suitable foaming techniques, such agitation, blowing, homogenization, aerosol, shaking, etc.

In one embodiment, the hydration liquid of the hydration foam may be a solution that includes the liquid for hydrating the device (e.g., water) along with additives and agents. The solution may include a liquid (e.g., water) at between 80 wt % and 99 wt % of the solution with the balance being any suitable additives and agents, such as those discussed herein. In another embodiment, the hydration liquid is greater than 80 wt % of the solution with the balance being additives and agents. In a further embodiment, the liquid is greater than or equal to about 90 wt % of the hydration medium.

In one embodiment, the hydration liquid, and thus the hydration foam, may include a surface tension reducing agent, which may assist in adding or incorporating gas bubbles into the hydration liquid to form the hydration foam. The surface tension reducing agent may be a foaming agent. In one embodiment, the surface tension reducing agent may be a surfactant or a mixture of surfactants. Furthermore, the surface tension reducing agent may be ionic or non-ionic. Examples of surface tension reducing agents include, but are not limited to, one or more of saponified coconut oil, vitamin E, polyoxyethylene sorbitan monolaurate, sodium methyl cocoyl taurate, sodium dodecyl sulfate, tween 20, tween 80, polysorbate, L-α-phosphatidylcholine, lecithin, stearyl stearate, sodium stearate, sodium laurate, sodium myristate, sodium myristate, sodium palmitate, sodium oleate, polyethylene glycol monododecyl ether, glycolic acid ethoxylate lauryl ether, glycolic acid ethoxylate oleyl ether, ethylene glycol monododecyl ether, polyoxyethylene glycerol ester, polyglyceryl esters, diglyceryl diisostearate, diglyceryl monolaurate, diglyceryl monooleate, Docusate sodium, dioctyl sulfosuccinate sodium salt, dioctyl sodium sulfosuccinate, sodium dodecylbenzenesulfonate, perfluorobutane sulfonic acid, 3-sulfopropyl ethoxylate lau-rylphenly ether, lauric acid sodium salt, N-aclylsarcosine sodium salt, N-lauroylsarcosine sodium salt.

The surface tension reducing agents may also provide health benefits to human tissue that come into contact with the hydrated device. For example, in a hydrophilic urinary catheter, the surface tension reducing agent may also serve to provide health benefits to the urinary tract, the stratum corneum and/or the bladder. Furthermore, the surface tension reducing agent may be in an amount of between about 0.05 wt % and about 5 wt % of hydration foam, which the balance being water and, optionally, other additives. In one embodiment, the hydration medium may include water at between about 95 wt % and 95.5 wt % and a surface tension reducing agent between about 0.05 wt % and about 5 wt %.

The hydration liquid, and thus the hydration foam, may also include a viscosity increasing agent that increases the viscosity of the hydration liquid within the foam. Examples of viscosity increasing agents include, but are not limited to, glycerol, polyethylene glycol, sugar alcohols, polyols, sugars, soluble polymers including polysaccharides, polyvinylpyrrolidone, polyethylene oxide, cationic or anionic polyelectrolytes including polyampholytes. Furthermore, the viscosity increasing agent may be in an amount between about 0.05 wt % and about 10 wt % of the liquid forming the hydration foam.

The hydration liquid, and thus the hydration foam, optionally, may also include a foam stabilizer that stables the foam, e.g., slows coalescence of the foam and release gas. Examples of foam stabilizers include by are not limited to Xanthan gum, guar gum, galactomannans, glucomannans, agar, carrageenan gum, polysaccharides. The foam stabilizer may be in an amount between about 0.01 wt % and about 5 wt % of the liquid forming the hydration foam. Optionally, the foam stabilizer may be any of the above-discussed mucilage compounds. When the hydration foam includes a mucilage compound, after the gas has been released from the foam, the hydration foam may form a mucilage layer over the hydrophilic material of the medical device, as discussed above.

In one embodiment, the hydration liquid that forms the foam may include about 0.05 wt % to 5 wt % of a surfactant (e.g., sodium dodecyl sulphate or sodium methyl cocoyl taurate), about 0.5 wt % to 10 wt % of a viscosity increasing agent (e.g., a polyol, such as glycerol), about 80 wt % to 99.0 wt % liquid for hydrating the device (e.g., water or de-ionized water), and about 0.01 wt % to 2 wt % stabilizer (e.g., Xanthan gum). In one embodiment, the hydration liquid that forms the foam may include about 0.1 wt % sodium dodecyl sulphate (SDS) or sodium methyl cocoyl taurate (SMCT), about 0.2 wt % xantham gum, about 1 wt % glycerol and about 98.7 wt % water. Optionally, the hydration liquid may also include about 0.1 wt %-15 wt % of a deep eutectic liquid or components that form a deep eutectic liquid. Also optionally, the hydration liquid may include between about 0.01 wt % and about 0.3 wt % trehalose, such a Trehalose dehydrate. When the foam is formed from the liquid, the balance of the foam is a gas. In one embodiment, the liquid that forms the hydration foam includes:

| | |
|---|---|
| Water | 80 wt % to 99.5 wt % |
| Surfactant (SMCT) | 0.01 wt % to 5 wt % |
| Polyol (glycerol) | 0.1 wt % to 10 wt % |
| Stabilizer (Mucilage, Xanthan gum) | 0.01 wt % to 2 wt % |
| DEL Forming Additive (Trehalose) (optional) | 0.01 wt % to 2 wt % |

The above liquid could be used in a foamed or unfoamed state.

In one method of making a foam, the surface tension reducing agent (e.g. sodium dodecyl sulphate), viscosity increasing agent (e.g. glycerol) and hydration liquid (e.g. water) are homogenized to form a foam. The foam may be for example at a about a 1 to 7 to about a 2 to 7 ratio in volume liquid to air bubbles or have foam density of 0.1 to 0.5 g/cm$^3$. The ratio or foam density may be higher or lower depending on package or sleeve size. Optionally, a foam stabilizing agent (e.g. mucilage, such as Xanthan gum) may be added and the foam may again be homogenized. The formation of the foam may be carried out at 23° C. In other embodiments, the formation may be carried out at higher or lower temperatures depending on the desired foam. For example, certain surface tension reducing agents readily create more bubbles at higher temperatures.

As described in more detail below, after the hydration foam is formed, it may then be placed in a package with a device, such as a hydrophilic urinary catheter assembly. The foam may include a density and fluid content tailored to fill the void of the package or other space containing the device, such that the required mass of fluid may be distributed evenly along the device. For example, the foam may be tailored to be distributed along the full length of a hydrophilic urinary catheter so that the catheter may be uniformly hydrated. Additionally, the foam also may allow for a sufficient amount of hydration liquid to be placed in the package without having to include excess hydration liquid. In one embodiment, the foam may be stable for about 4 hours or greater than 4 hours. That is, it may take about 4 hours for the foam to start to dissipate. In other embodiments, the foam may be stable for a longer or shorter time period.

Furthermore, using a hydration foam has some advantages. For example, the foam is visually perceivable and it is easily to observe during manufacturing of the product. For instance, it is easy for a person or electronic eye to visually observe the amount and location of foam during manufacturing. Additionally, because the foam occupies a greater volume than liquid alone, using a foam results in less liquid being used to hydrate a given surface area or device. Also, because the foam eventually dissipates, it is not visible or readily perceived by the end user. Optionally, the foam may not dissipate and is visible to the end user.

FIGS. 11-14 illustrate hydration foam forming and delivery systems. Turning to the system 200 illustrated in FIG. 11, the system 200 includes or is fed a supply of a hydration liquid 202, which may be any suitable hydration liquid, such as those described herein. A pump 204 in-line with the supply of hydration liquid 202 pumps the hydration liquid through a flow meter 206, which meters the flow of the hydration liquid. The system 200 also includes or is fed a supply of gas 208, which may be for example ambient air, nitrogen or a mixture of both. The gas also may be any other suitable gas. The gas flows through a pressure regulator 210 and a flow meter 212. The gas then flows through a sintered nozzle 214 where it is mixed with the hydration liquid. As represented at 216, the flow meter 206 and flow meter 212 may be in communication with each other and may be adjusted as needed to regulate the amount of hydration liquid and amount of gas being mixed. The gas and hydration liquid then flow through a homogenizer 218 to induce the forming of the foam. A recirculation loop around homogenizer maybe included to increase homogenization tendency i.e. breakdown of air/gas bubbles. The foam is then metered out or dosed by a metering/dosing pump 220. A sampling point or port 222 may be located between the homogenizer 218 and metering/dosing pump 220. The port 222 may include a valve 223 for opening and closing the port. The dose of foam is delivered or injected into a catheter package or sleeved catheter assembly by a dispensing member 224, such as a docketing nozzle, port or needle.

Turning to the system 226 illustrated in FIG. 12, the system 226 includes or is fed a supply of a hydration liquid 228. A metering or dosing pump 230 in-line with the supply of hydration liquid 228 pumps a dose of the hydration liquid into a pressure chamber 232. The system 226 also includes or is fed a supply of gas 234, which may be for example, ambient air, nitrogen or a mixture of the two. The gas also may be any other suitable gas. The gas flows through a pressure regulator 236 and a flow meter 238. The metered gas then flows through a sintered nozzle 240 into the pressure chamber 232 where it is mixed with the hydration liquid. The pressure chamber includes a dispensing nozzle 242 which induces the creation of foam when the mixture of gas and hydration liquid passes therethrough. As represented at 243, the dosing member 230, flow meter 238 and dispensing nozzle 242 may be in communication with each other and may be adjusted as needed to regulate the amount of hydration liquid and amount of gas being mixed and the amount of foam being formed. The foam is then dispensed by the dispensing member 244 into a medical device assembly, such as a catheter package or a sleeved catheter assembly.

FIG. 13 illustrates a pressurized vessel 246 for dispensing foam. The vessel may be pressurized by a gas 247, such as air, nitrogen or a mixture of both. The foam 245 may be made by the systems described above or any other suitable system. After the form 245 is formed, it is pumped into the pressurized vessel 246. The vessel 246 includes an aerosol dispensing valve 248 and a dispensing member 250 for dispensing the foam 245 from the vessel 246 directly into a medical device assembly, such as a catheter package or sleeved catheter assembly. The dispensing member 250 may also be configured to deliver foam into a system that injects the foam into the package or sleeve. Forming the foam and then placing it into a pressure vessel for delivery allows for the foam to be formed at one location and then dispensed at another location. For example, the foam may be prepared outside of a clean room and then brought into the clean room in the pressurized dispensing vessel.

Figure 14:
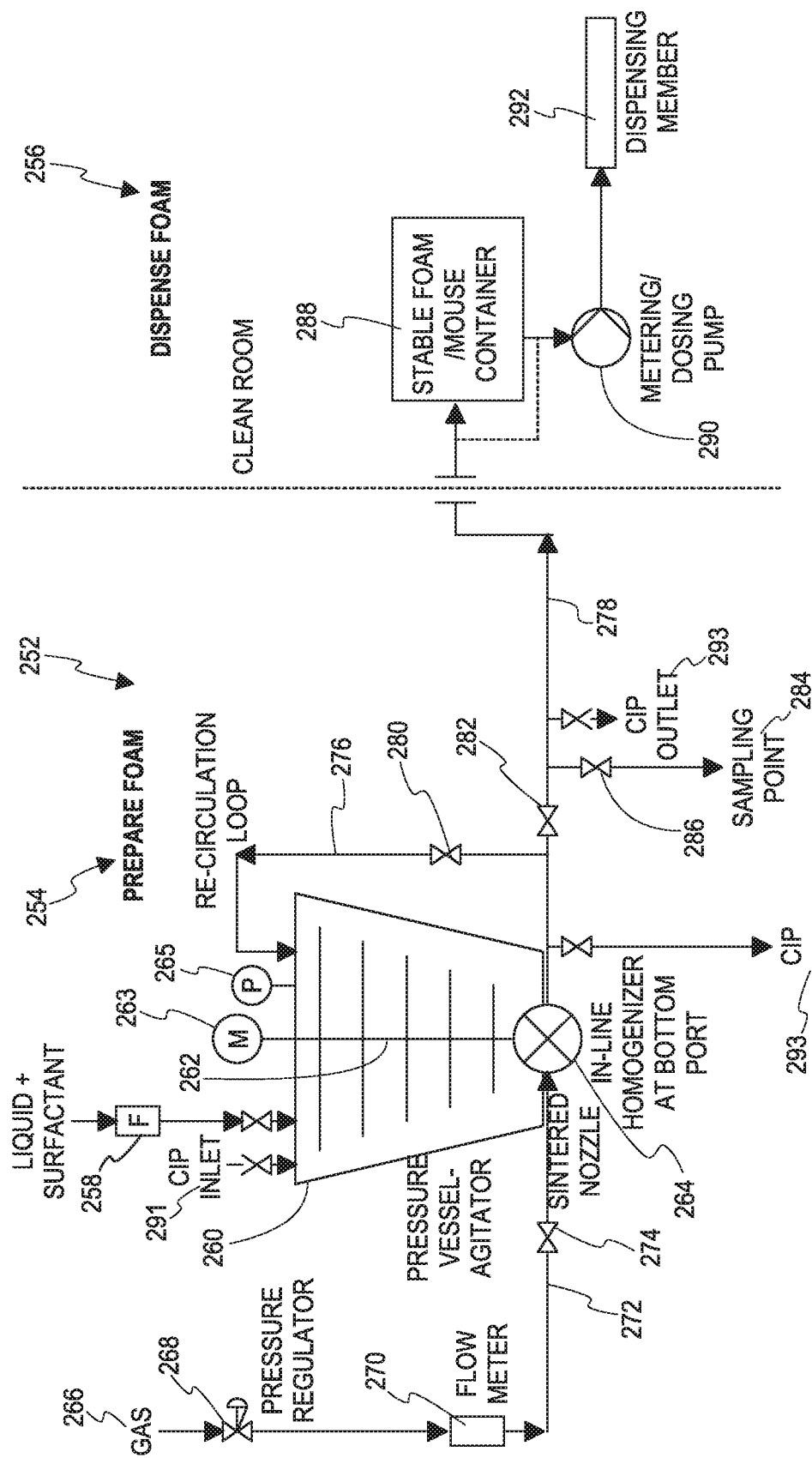
FIG. 14 a schematic illustration of another embodiment of a hydration foam forming and dispending system.

Turning to FIG. 14, this figure illustrates a system 252 that may be a clean in place (CIP). The system includes a foam preparation sub-system 254 and a foam dispensing sub-system 256. As shown in the drawings, the foam preparation sub-system 254 may be outside of the clean room or maybe included in the clean room and the foam dispensing sub-system 256 may be located in the clean room. The foam preparation sub-system 254 includes or is fed a supply of hydration liquid 258. The hydration liquid is fed into a mixing vessel 260 that has an agitator 262 to stir it. The agitator 262 may be actuated by a motor 263. The mixing vessel may also include a pressure indicator 265. The hydration liquid then flows into an in-line homogenizer 264 which is in communication with the vessel 260. The system also includes or is fed a gas from a supply of gas 266. The gas is fed into a pressure regulator 268 and then through a flow meter 270. The gas then flows through a flow path 272 and through a sintered nozzle 274 into the in-line homogenizer 264. The flow path 272 includes a valve 274 to open and close the flow path 272.

The gas and liquid mix in the homogenizer 264 to form a foam. The homogenizer 264 is in communication with a re-circulation flow path 276 and a dispensing flow path 278. The re-circulation flow path 276 recirculates the foam back to the mixing vessel 260 and the dispensing flow path 276 is in communication with dispensing sub-system 256. The re-circulation flow path 276 has valve 280 associated therewith and the dispensing flow path 278 has valve 282 associated therewith. When the foam is re-circulated, the valve 280 in the re-circulation flow path 276 is opened and the valve 282 in the dispensing flow path 278 is closed. The foam may be re-circulated through the re-circulation flow path 276 any number of desired times until it is sufficient for the desired use. Furthermore, if additional gas is desired during re-circulation, valve 274 will be opened. If additional homogenization is desired without any additional gas form the gas supply 266, valve 274 will be closed during re-circulation. When the foam is ready to be dispensed, the valve 280 in the re-circulation flow path is closed and the valve 282 in the dispensing flow path 278 is open. The dispensing flow path may also include a sampling point or port 284 so that the foam may be sampled prior to be dispensed. The sampling port 284 may also include a valve 286.

The foam flows through the dispensing flow path 278 to the dispensing sub-system 256. The foam may flow into a vessel 288, which may for example be similar to the above described pressure, and then to a metering or dosing pump 290. Alternatively, the foam may flow directly to the metering or dosing pump 290. The metering/dosing pump sends a metered amount or dose of foam to a dispensing member 292. The dispensing member 292 then dispenses the foam into a medical device assembly, such as a package or catheter sleeve.

The system 252, optionally, may include clean in place inlets ports 291 and outlet ports 293 that allow the system to be cleaned and flushed.

Turning to FIGS. 15-18, a foam hydration medium 310 (FIG. 16) may be formed within the package 300 through a chemical reaction. In some embodiments, the foam hydration medium 310 may be formed during the packaging process. In other embodiments, prior to use, the user may initiate the reaction that forms the hydration foam 310. The reaction may be a reaction of two or more chemicals that produce a gas, including but not limited to, carbon dioxide, nitrogen, etc. In one embodiment, the reactants may be sodium bicarbonate and citric acid. As explained in more detail below, the reactants may be in solution and/or in solid form.

FIGS. 15 and 16 illustrate a package 300 that has similar features to that of package 100 shown in FIGS. 5 and 6. As schematically shown in FIG. 15, during the manufacturing process, the hydrophilic catheter 312 is placed in the cavity of the package 300 and the foam forming reactants may be placed into the package just prior to the package being sealed. The foam forming reactants may be delivered as a solid or a solution. For example, referring to FIG. 15, during packaging of catheter 312, a first solution 302 containing a first reactant may be dispensed into the inner cavity of the catheter package 300 through a dispensing member or spout 304. A second solution 306 containing a second reactant may be dispensed into the inner cavity of the catheter package 300 through a dispensing member or spout 308. In one embodiment, the total amount of the two solutions dispensed into the package may be 4 ml or less. In one example, 2 ml or more of one of the solutions and 2 ml or less of the other solution may be dispensed into the package. In another example, 3 ml or less of one of the solutions and 1 ml or more of the other solution may be dispensed into the package.

After the first and second solutions 302 and 306 are dispensed, the package is sealed. When the first and second solutions 302 and 306 mix, the first and second reactants react with each other to release a gas to foam the solutions and form a hydration foam 310. As illustrated in FIG. 16, the foam 310 occupies the cavity of the package 300 and hydrates the hydrophilic material of the catheter 312.

In one example, one of the first solution 302 and the second solution 306 may be an aqueous solution of water and citric acid and the other of the first and second solutions may be an aqueous solution of water and sodium bicarbonate. One or both of the first and second solutions may include a surface tension reducing agent (such as a foaming agent), a foam stabilizing agent, and/or a viscosity increasing agent, such as any of the agents listed above. For example, the first and/or second solution may include sodium dodecyl sulfate, xanthan gum and glycerol. Additionally, the agents in the foam may be in any of the amounts listed above. In one exemplary embodiment, the first solution may include citric acid, a tension reducing agent, a foam stabilizing agent, and/or a viscosity increasing agent, and the second solution may include sodium bicarbonate. In another embodiment, the first solution may include citric acid and the second solution may include sodium bicarbonate, a tension reducing agent, a foam stabilizing agent, and/or a viscosity increasing agent. In yet another embodiment, the first solution may include citric acid and, for example, sodium dodecyl sulfate, xanthan gum, glycerol and water and the second solution may include sodium bicarbonate and water. Alternatively, the main foaming components of the hydration solution may be reversed as that the first solution may include citric acid and water, and the second solution may include sodium bicarbonate and for example sodium dodecyl sulfate, xanthan gum, glycerol and water. Or further still any mixture of sodium dodecyl sulfate, xanthan gum, glycerol and water may be combined with the citric acid solution or with the sodium bicarbonate solution, whilst keeping the foaming reagents separate.

In another method of making the catheter product, the first and second reactants may be placed in the package in solid form. They may be combined in one solid form (such as one tablet) or two different solid forms (two tablets or two loose powders). For example, citric acid and sodium bicarbonate may be placed in the package in solid form. When the hydration liquid is dispensed into the package, the solid forms dissolve into solution and the reactants react to form the hydration foam. The hydration liquid may include any of the above mentioned agents. In another embodiment, one of citric acid or sodium bicarbonate may be in solid form and the other may be in a solution that is dispensed into the package.

Figure 19:
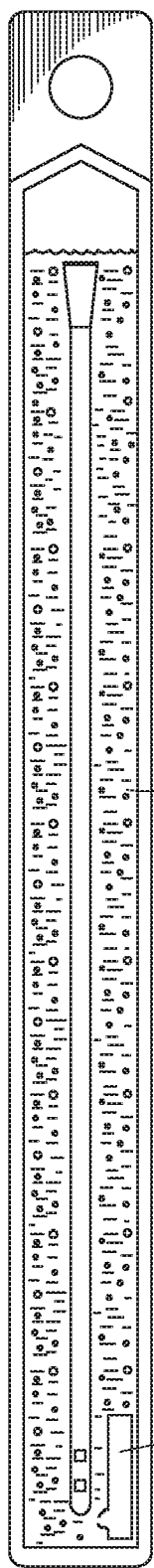
FIG. 19 is a front plan view of the catheter package of FIG. 17 showing the hydration foams occupying the cavity of the catheter.

FIGS. 17-19 illustrate another embodiment of a package 300a that includes a hydrophilic catheter 312a, a first solution 302a containing a first reactant and a second solution 306a containing a second reactant. The first and second reactants, when mixed, react to produce a gas that foams the solutions to form a hydration foam that hydrates the hydrophilic material of the catheter. The reactants may be any of the above mentioned reactants. Also, the first and/or the second solutions may include one or more of a surface tension reducing agent (such as a foaming agent), a foam stabilizing agent, and/or a viscosity increasing agent, such as any of the agents listed above.

The first solution 302a and the second solution 306a may be separated within the cavity of the package 300a until a desired time. In one embodiment, the first solution 302a may be loose within the package 300a and the second solution 306a may be contained within a sealed compartment 308a that may be opened at a desired time to allow mixing of the first and second solutions. For example, the compartment 308a may be burstable or otherwise openable. In the illustrated embodiment, the compartment 308a is a burstable sachet that may be burst by the application of pressure. The sachet may be burst by applying pressure to the sachet through the package. For example, the sachet may be squeezed between the hand or fingers, or between the hand and a stationary object (e.g., table top, user's leg, etc.) the compartment 308a may be opened during the manufacturing process or prior to distribution to the user. Alternatively, the compartment may be opened by the user just prior to use.

Referring to FIGS. 18 and 19, when the compartment 308a is opened, the solutions mix and the reactants react to form a foam 310a. For example, when the compartment 308a is a sachet, the sachet is burst open by pressure to release the second solution 306a. The second solution 306a mixes with the first solution 302a and a foam is formed.

Figure 20:
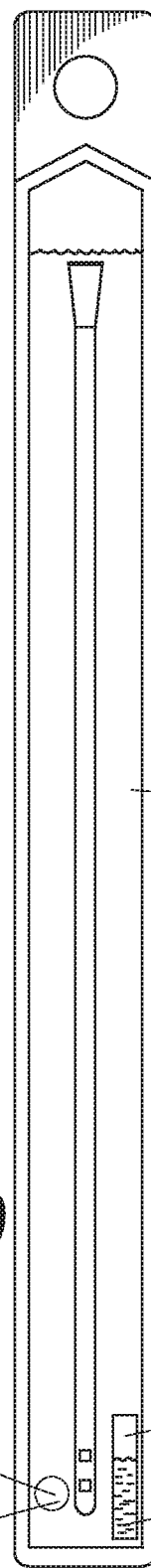
FIG. 20 is another embodiment of a catheter package that includes reactants to form a hydration foam.

FIG. 20 illustrates another embodiment which the reactants are in a solid form 314b within the package and a hydration liquid 316b is within an openable compartment 308b. The reactants may be a in a single tablet 318b, may be in two different tablets or may be in powder form. The hydration liquid 316b may include one or more of a surface tension reducing agent (such as a foaming agent), a foam stabilizing agent, and/or a viscosity increasing agent, such as any of the agents listed above. When the compartment 308b is opened, the reactants dissolve within the hydration liquid 316b and react to form a gas that foams the hydration liquid to create a hydration foam that fills or occupies the cavity of the package, similar to that shown in FIG. 19.

FIGS. 21-41 illustrate additional systems and methods for delivering and/or forming a foamed hydration medium within the sleeve or package of a catheter product. The hydration medium or liquid may be any of those disclosed herein.

Figure 21:
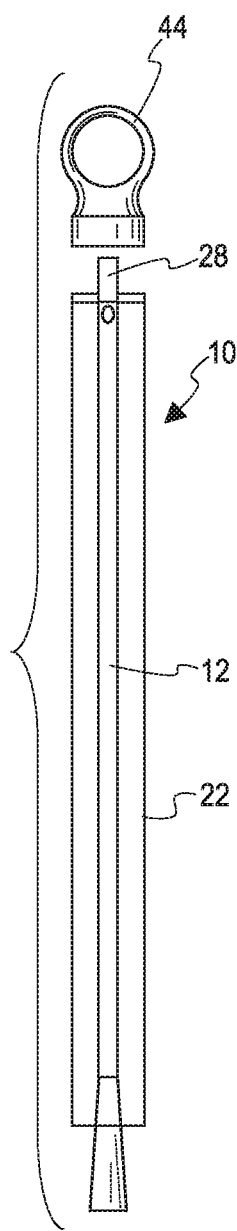
FIG. 21 is a front plan view of a catheter assembly shown with the protective cap removed.
Figure 22:
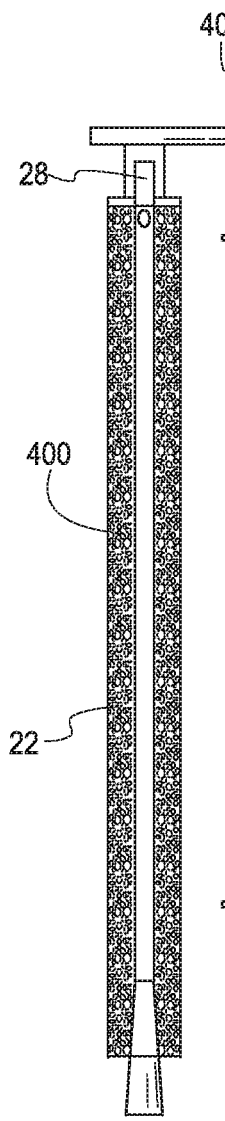
FIG. 22 is a front view of the catheter assembly and a delivery system, showing hydration foam being delivered into the sleeve of the assembly.

Turning to FIGS. 21 and 22, similar to FIG. 1, the catheter assembly 10 has a sleeve 22 surrounding a catheter 12. Referring to FIG. 22, the system for delivering hydration foam into the interior cavity of the sleeve 22 includes an on-demand foaming device that may be used by the end user during the catheterization procedure. The system may include an aerosol container 402 that contains a liquid hydration medium under pressure with air or gas, which may be, but is not limited to, nitrogen, carbon dioxide, nitrous oxide, etc. The aerosol container 402 also includes a release valve 404 that releases the foam 400 from the aerosol container 402. The aerosol container 402 also includes a nozzle 406 that is configured to dock with, engage or otherwise operatively connect with the proximal end of the sleeve, or the insertion aid 28, if present. The nozzle 406 delivers the hydration foam 400 into the sleeve 22. Optionally, the aerosol container 402 also may include a metering device for metering the amount or dose of foam dispensed into the sleeve.

In use, the user removes the cap 28 from the catheter assembly 10, if a cap is present. The nozzle 406 and proximal end of the sleeve 22 are engaged, and the user opens valve 404 to release the foam 400. The aerosol container 402 may include a button that when depressed opens the valve 404. When the compressed liquid and air/gas mixture is released from the nozzle 406 it results in formation of foam 400. The type of foam and volume can be control by the nozzle type. Optionally, a venturi tube or widget within the container or nozzle can form the foam, i.e. mix the air/gas and liquid compositions. After the foam 400 has been added to the sleeve 22, the user waits for the hydrophilic coating to be sufficiently hydrated (about 2 minutes). The catheter is then ready for use.

Figure 23:
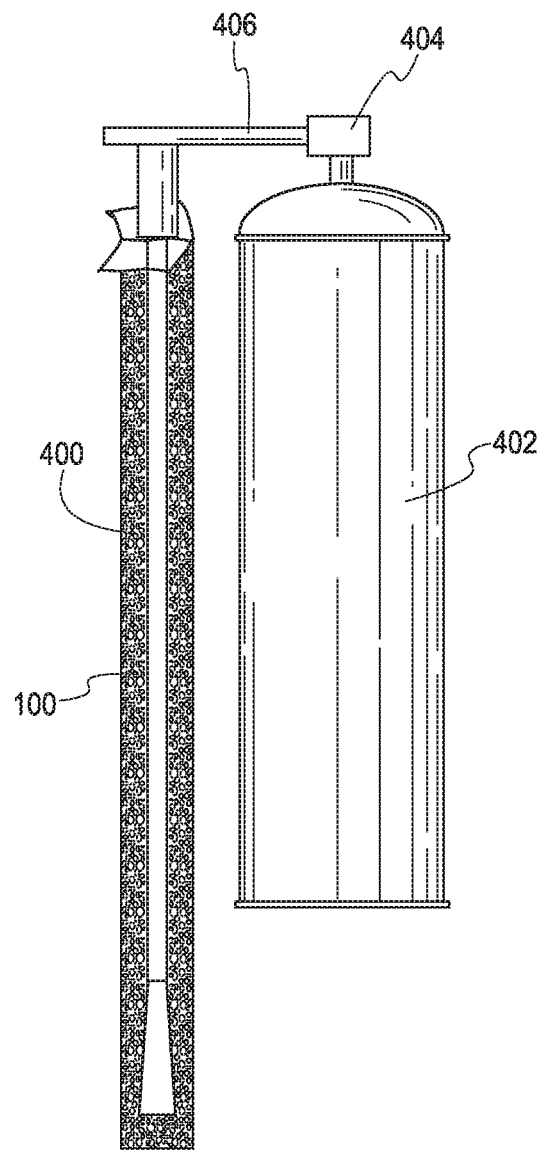
FIG. 23 is a front view of a packaged catheter product and a delivery system, showing hydration foam being delivered into the sleeve of the assembly.

Turning to FIG. 23, in this embodiment, the aerosol container 402 may be used to deliver foam 400 into package 100, which is similar to the package of FIG. 5. In use, the user peels or tears open the package 100 and then inserts the nozzle 406 into the opening or connects the nozzle 406 to the package 100. Then, the user opens valve 404 to release the foam 400 and deliver it from the nozzle 406 and into the package 100.

Figures 24, 25:
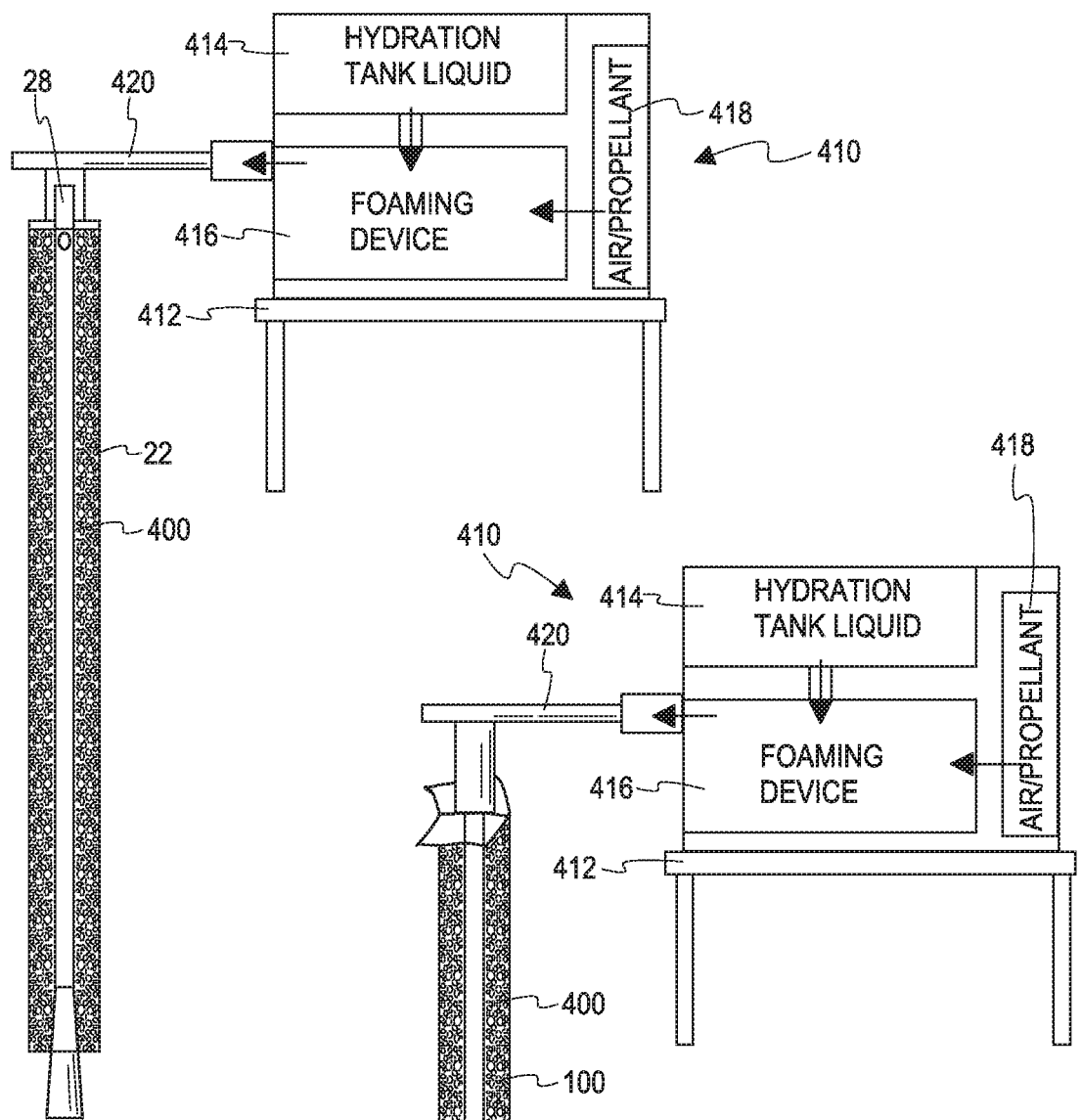
FIG. 24 is a front view of the catheter assembly and a delivery system, showing hydration foam being delivered into the sleeve of the assembly.
FIG. 25 is a front view of a packaged catheter device and a delivery system, showing hydration foam being delivered into the sleeve of the assembly.

FIGS. 24 and 25 illustrate another embodiment of a foam delivery system 410. The system 410 may be a table-top system that is configured to sit on a table-top or counter 412. While the aerosol container 402 (FIGS. 21-24) provides for portable on-the-go usage, the system 410 may be designed for at-home usage. The system 410 could also be configured for on-the-go usage. The system 410 includes a tank 414 for holding hydration liquid and a foaming device 416. The tank 414 may be a refillable tank or an exchangeable tank. The foaming device 416 may include an agitator or homogenizer that mixes controlled volumes of liquid and gas to form foam. Optionally, the system may include a chamber of gas 418. The chamber of gas 418 also may be refillable or exchangeable. Alternatively, the mixing device 416 may have an ambient air intake (not shown). The tank 414 of liquid and the source of gas 418 are connected to the foaming device 416, and the foaming device 416 may include meters and valves to regulate the liquid to gas ratio entering the foaming device 416.

Referring to FIG. 24, the system 410 may include a nozzle 420 that engages or connects with the proximal end of the sleeve 22, or the insertion aid 28, if present. After the nozzle 420 is engaged, the system 410 is activated to deliver foam 400 into the sleeve 22. Referring to FIG. 25, the nozzle 420 may engage the opening of package 100 or be inserted into the opening, after which, the system is activated to deliver foam 400 into the package 120.

Figure 26:
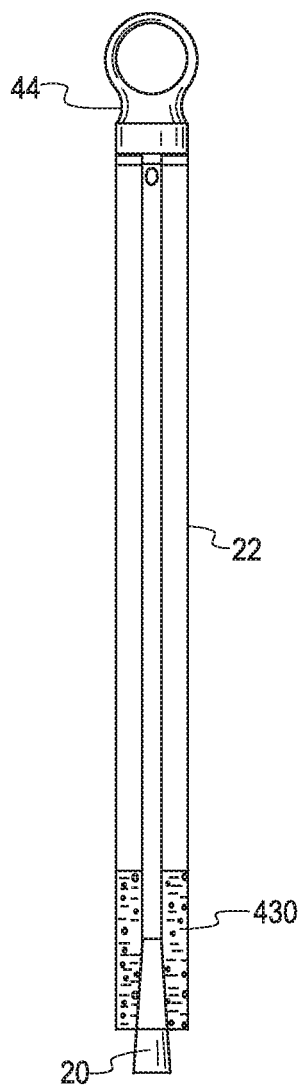
FIG. 26 is a front plan view of a catheter assembly.
Figure 27:
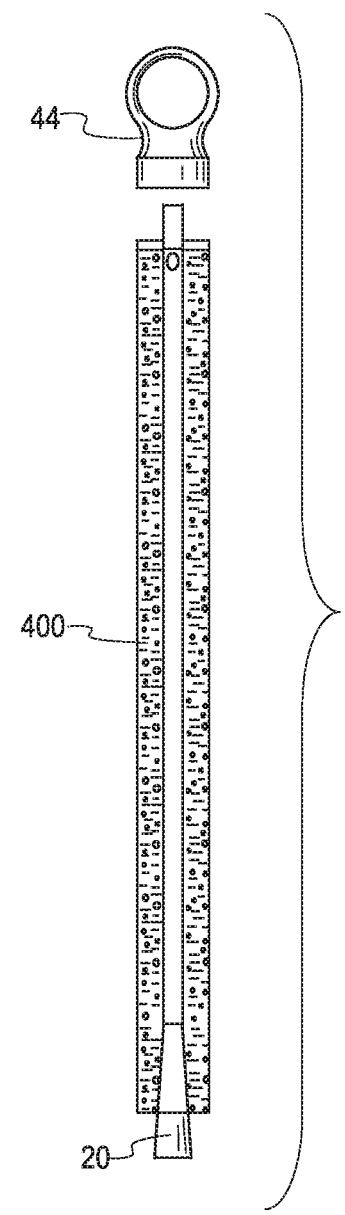
FIG. 27 is a front plan view of the catheter assembly of FIG. 26, shown with the protective cap removed and foam within the sleeve.

Referring to FIGS. 26 and 27, the hydration medium is a liquid 430 that is saturated or supersaturated with a gas, such as carbon dioxide, nitrogen, nitrous oxide, etc. The saturated/supersaturated liquid is injected into the sleeve 22 under pressure and the sleeve 22 is sealed. The funnel 20 and cap 44 each may include a removable seal that assists in making the interior of the sleeve 22 air tight or closed to the ambient atmosphere. Opening the interior cavity of the sleeve 22 to the ambient atmosphere results in the supersaturated or saturated liquid 430 being under atmospheric conditions and a change in pressure. This change from a high to a low pressure results in the release of gas from the liquid. The released gas foams the liquid to create foam 400, which expands within the sleeve 22 and contacts the catheter. The interior cavity of the sleeve may be opened to the atmosphere by removal of cap 44 or removal of the seal from the funnel 20. The volume of foam and its stability are dependent upon pressure, type of gas and liquid volume.

Figure 28:
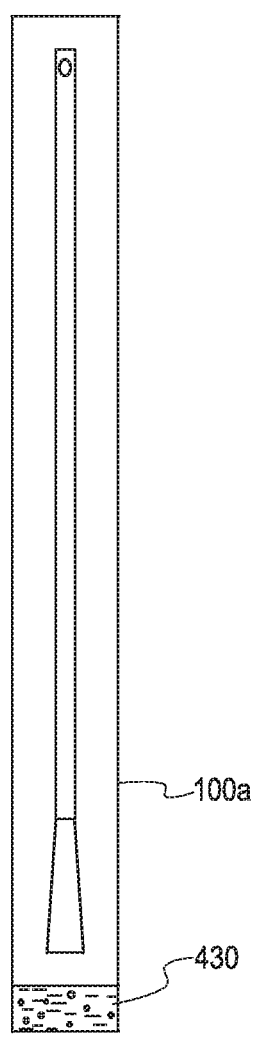
FIG. 28 is a front plan view of a packaged catheter product.
Figure 29:
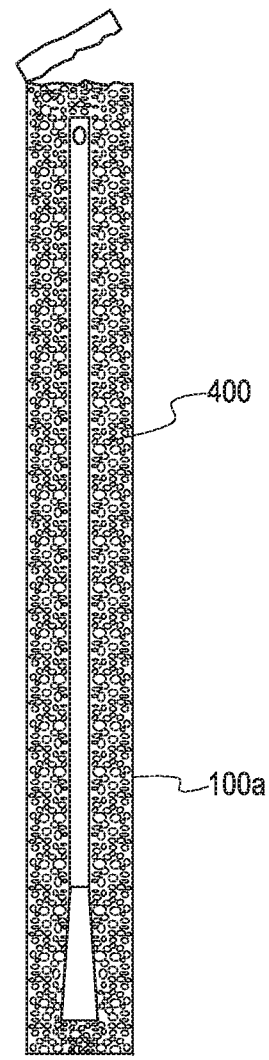
FIG. 29 is a front plan view of the packaged catheter product of FIG. 28, shown with the package in opened and foam within the package.

Referring to FIGS. 28 and 29, a saturated/supersaturated liquid 430 is injected into the package 100a under pressure and the package is sealed. Opening of the package 100a, results in the supersaturated or saturated liquid 430 being under atmospheric conditions and a change in pressure. This change from a high to a low pressure results in the formation of foam 400, as described above. The foam 400 expands within the package 120 and contacts the catheter.

Figures 30, 31:
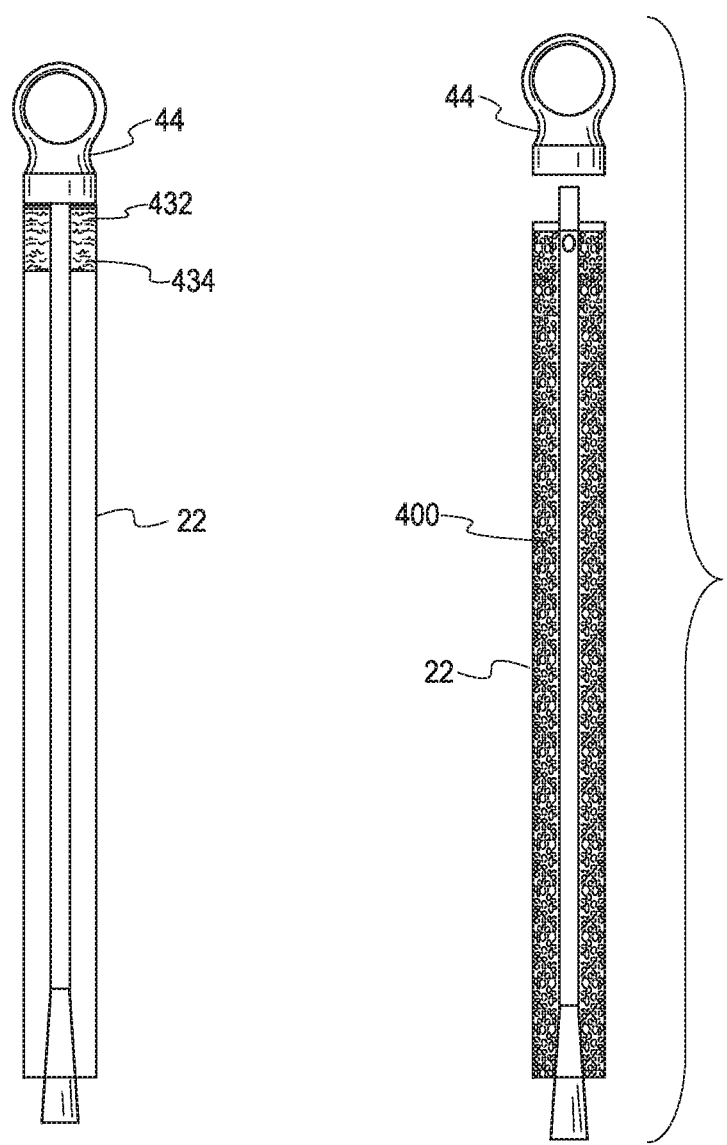
FIG. 30 is a front plan view of a catheter assembly.
FIG. 31 is a front plan view of the catheter assembly of FIG. 30, shown with the protective cap removed and foam within the sleeve.

Turning to FIGS. 30 and 31, a compartment 432, such as a sachet, of a saturated/supersaturated liquid 434 is located within the sleeve 22. The opening of the compartment 432 results in the supersaturated or saturated liquid 434 being under atmospheric conditions and a change in pressure. This change from a high pressure to a low pressure results in the formation of foam 400 that expands within the sleeve 22 and contacts the catheter. The compartment 432 may be opened by any suitable method, such as bursting or tearing. For example, the cap 44 and compartment 432 may be configured such that when the cap 44 is removed from the assembly, the compartment 432 is opened. The compartment 432 may include a tear strip that is attached to the inside of the cap 44 such that when the cap 44 is removed, it pulls the tear strip and opens the compartment 432.

Figures 32, 33:
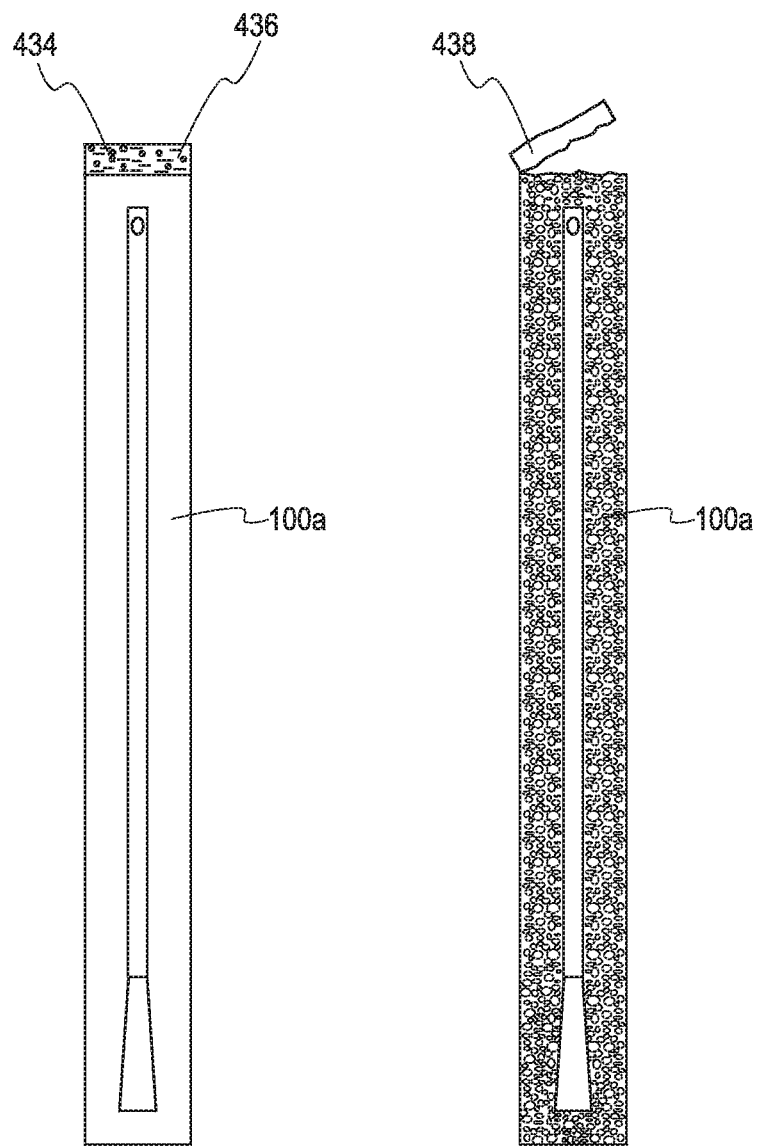
FIG. 32 is a front plan view of a packaged catheter device.
FIG. 33 is a front plan view of the packaged catheter device of FIG. 32, shown with the package opened and foam within the package.

Turning to FIGS. 32 and 33, a compartment 436 of a saturated/supersaturated liquid 434 is located within the package 100a. The compartment 436 may be opened by any suitable method, such as by bursting or tearing. For example, the compartment 436 and package 100a may be configured such that when the package 100a is opened, the compartment 436 is opened. The compartment 436 may include a tear line that is in line with a tear line 438 of the package 100a such that when the package 100a is torn open, the compartment 436 is also torn open.

Turning to FIGS. 34-35 and 36-37, in these catheter products, the foam 400 is formed within the sleeve 22 or package 100a as a result of a chemical reaction. Similar to that described above with respect to FIGS. 15-18, the reaction may be a reaction of two or more chemicals that produce a gas, including but not limited to, carbon dioxide, nitrogen, etc. In one embodiment, the reactants may be sodium bicarbonate and citric acid, both of which may be in solution and/or in solid form. In each of the products, optionally, one of the chemicals is contained in a first compartment 440 and the other of the chemicals is contained in a second compartment 442. One of the first and second compartments 440/442 includes the chemical in a solution and the other one includes the chemical in solution or solid form. In another embodiment, one of the first and second compartments includes both of the chemicals and the other of the compartments includes the hydration liquid.

Figures 34, 35:
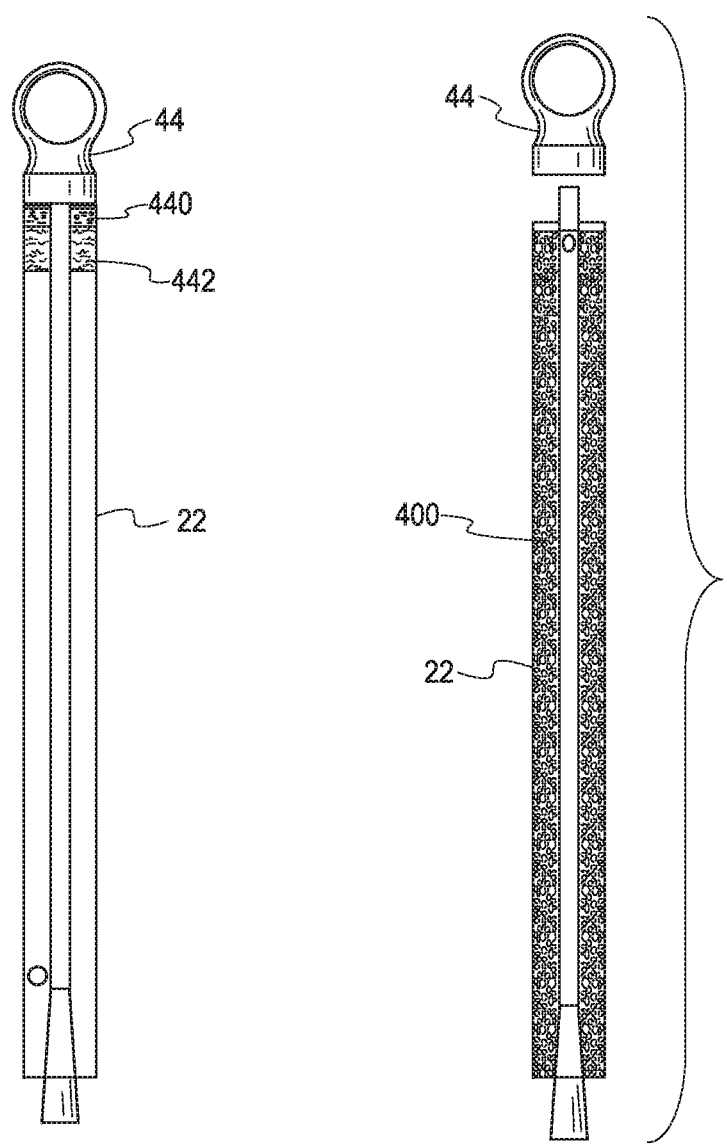
FIG. 34 is a front plan view of a catheter assembly.
FIG. 35 is a front plan view of the catheter assembly of FIG. 34, shown with the protective cap removed and foam within the sleeve.
Figure 36:
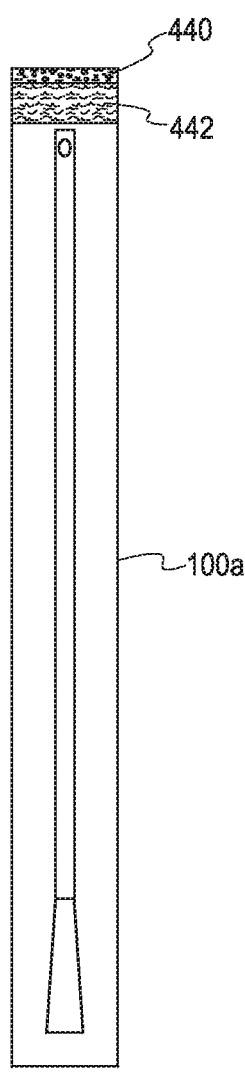
FIG. 36 is a front plan view of a packaged catheter product.
Figure 37:
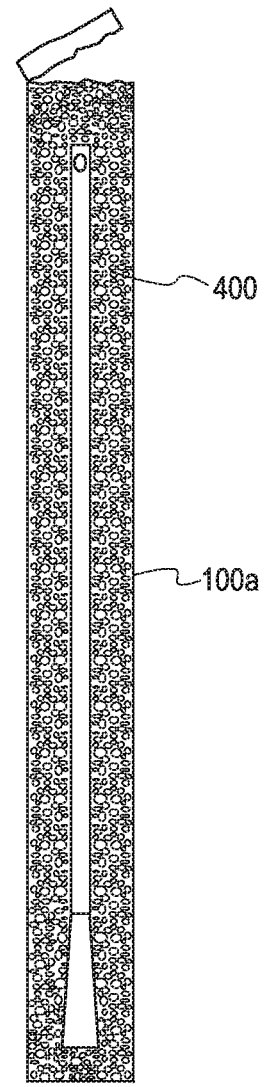
FIG. 37 is a front plan view of the packaged catheter product of FIG. 36, shown with the package in opened and foam within the package.
Figure 38:
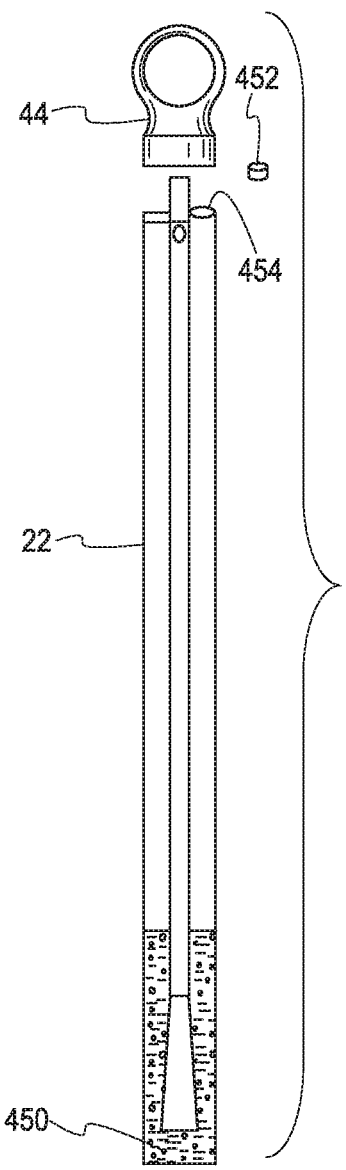
FIG. 38 is a front plan view of a catheter assembly.
Figure 39:
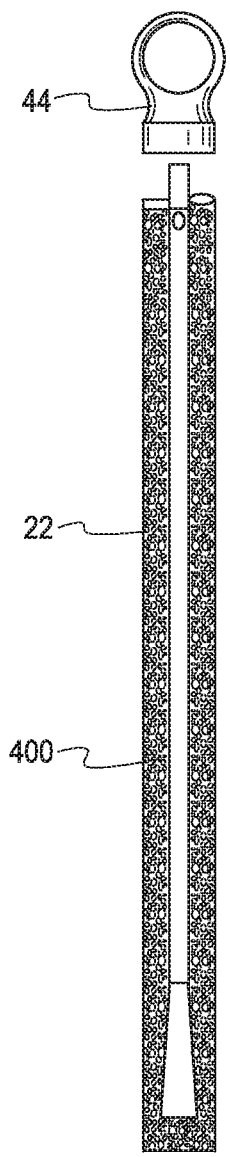
FIG. 39 is a front plan view of the catheter assembly of FIG. 38, shown with the protective cap removed and foam within the sleeve.
Figures 40, 41:
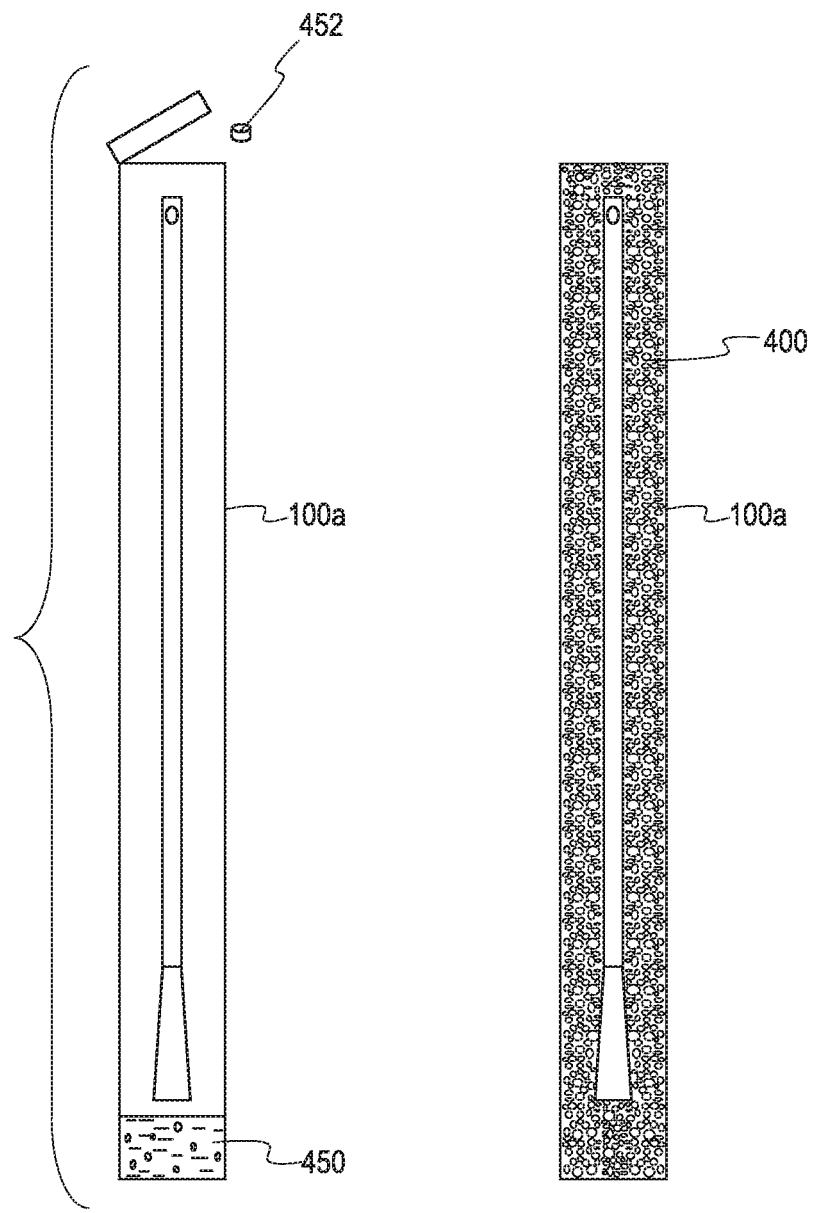
FIG. 40 is a front plan view of a packaged catheter product.
FIG. 41 is a front plan view of the packaged catheter product of FIG. 40, shown with the package in opened and foam within the package.

When the cap 44 is removed from the sleeved assembly in FIGS. 34 and 35 or the package 100a is opened in FIGS. 26 and 37, the first and second compartments 440/442 are opened. When the compartments 440/442 open, the chemicals mix in the liquid and form a gas that foams the liquid, resulting in hydration foam 400. The foam 400 expands within the sleeve 22 or package 100a and contacts the hydrophilic coating of the catheter to hydrate the same.

Turning to FIGS. 38-39 and 40-41, in these products, the sleeve 22 or package 100a contains a hydration liquid 450. After the sleeve 22 or package 100a is opened, the user delivers a form foaming solid, such as a tablet 452, into the sleeve 22 or package 100a. In the sleeved assembly shown in FIGS. 38 and 39, the sleeve 22 includes an opening 454 for delivering the tablet 452 into the sleeve 22. In the package 100a shown in FIGS. 40 and 41, the user delivers the tablet 452 through the opening 456 formed during opening of the package 110a.

The reactants, such as those discussed above, may be in a single tablet. When delivered into the sleeve or package, the reactants dissolve within the hydration liquid and react to form a gas that foams the hydration liquid to create a hydration foam that fills or occupies the cavity of the sleeve or package.

It will be understood that the embodiments described above are illustrative of some of the applications of the principles of the present subject matter. Numerous modifications may be made by those skilled in the art without departing from the spirit and scope of the claimed subject matter, including those combinations of features that are individually disclosed or claimed herein. For these reasons, the scope hereof is not limited to the above description but is as set forth in the following claims, and it is understood that claims may be directed to the features hereof, including as combinations of features that are individually disclosed or claimed herein.

The invention claimed is:

1. A urinary catheter product, comprising:
a package containing a hydrophilic urinary catheter and a foamed hydration medium for hydrating a hydrophilic material of the urinary catheter.

2. The urinary catheter product of claim 1, wherein the foamed hydration medium comprises a hydration liquid and a mass of bubbles formed in the hydration liquid.

3. The urinary catheter product of claim 2, wherein the mass of bubbles are formed from air or gas.

4. The urinary catheter product of claim 3, wherein the hydration liquid to the air or gas volume ratio is about 1 to 7 to about 2 to 7.

5. The urinary catheter product of claim 2, wherein the hydration liquid comprises water.

6. The urinary catheter product of claim 2, wherein the hydration liquid comprises a solution wherein water is greater than about 80 wt % of the hydration liquid.

7. The urinary catheter product of claim 1, wherein the foamed hydration medium further comprises a surface tension reducing agent.

8. The urinary catheter product of claim 7, wherein the surface tension reducing agent comprises a foaming agent.

9. The urinary catheter product of claim 7, wherein the surface tension reducing agent comprises a surfactant.

10. The urinary catheter product of claim 7, wherein the surface tension reducing agent is ionic or non-ionic.

11. The urinary catheter product of claim 7, wherein the surface tension reducing agent comprises one or more of saponified coconut oil, vitamin E, polyoxyethylene sorbitan monolaurate, sodium dodecyl sulfate, tween 20, tween 80, polysorbate, L-α-phosphatidylcholine, lecithin, stearyl stearate, sodium stearate, sodium laurate, sodium myristate, sodium myristate, sodium palmitate, sodium oleate, polyethylene glycol monododecyl ether, glycolic acid ethoxylate lauryl ether, glycolic acid ethoxylate oleyl ether, ethylene glycol monododecyl ether, polyoxyethylene glycerol ester, polyglyceryl esters, diglyceryl diisostearate, diglyceryl monolaurate, diglyceryl monooleate, Docusate sodium, dioctyl sulfosuccinate sodium salt, dioctyl sodium sulfosuccinate, sodium dodecylbenzenesulfonate, perfluorobutane sulfonic acid, 3-sulfopropyl ethoxylate lau-rylphenly ether, lauric acid sodium salt, N-acylsarcosine sodium salt, and N-lauroylsarcosine sodium salt.

12. The urinary catheter product of claim 7, wherein the surface tension reducing agent is present in an amount of between about 0.01 wt % and about 5 wt % of the foamed hydration medium.

13. The urinary catheter product of claim 1, wherein the foamed hydration medium comprises a viscosity increasing agent.

14. The urinary catheter product of claim 13, wherein the viscosity increasing agent comprises one or more of glycerol, polyethylene glycol, sugar alcohols, polyols, polysaccharides and sugars.

15. The urinary catheter product of claim 13, wherein the viscosity increasing agent is present in an amount between about 0.1 wt % and about 10 wt % of the foamed hydration medium.

16. The urinary catheter product of claim 1, wherein the foamed hydration medium further includes a foam stabilizer.

17. The urinary catheter product of claim 16, wherein the foam stabilizer comprises one or more of xanthan gum, guar gum, galactomannans, glucomannans, agar, carrageenan gum, polysaccharides, and polyvinylpyrrolidone.

18. The urinary catheter product of claim 16, wherein the foam stabilizer is present in an amount between about 0.01 wt % and about 2 wt % of the foamed hydration medium.

19. The urinary catheter product of claim 16, wherein the foam stabilizer is mucilage.

20. The urinary catheter product of claim 1, wherein the foamed hydration medium includes components of a deep eutectic liquid.

21. The urinary catheter product of claim 20, wherein at least one of the components comprises trehalose.

22. The urinary catheter product of claim 1, wherein the foamed hydration medium further comprises a cryoprotectant.

23. The urinary catheter product of claim 3, wherein a density of the foamed hydration medium is from 0.1 to 0.5 g/cm$^3$.

24. The urinary catheter product of claim 3, wherein a density of the foamed hydration medium is from about 0.16 to 0.3 g/cm$^3$.

* * * * *